United States Patent [19]

Larsen et al.

[11] Patent Number: 5,132,424

[45] Date of Patent: Jul. 21, 1992

[54] PYRAZOLO-PYRROLO-PYRIMIDINE-DIONES

[75] Inventors: Scott D. Larsen, Kalamazoo; Frank P. Bell, Vicksburg, both of Mich.

[73] Assignee: The Upjohn Company, Kalamazoo, Mich.

[21] Appl. No.: 571,564

[22] PCT Filed: Jul. 3, 1989

[86] PCT No.: OCT/US89/02854

§ 371 Date: Jan. 21, 1991

§ 102(e) Date: Jan. 21, 1991

[87] PCT Pub. No.: WO90/01031

PCT Pub. Date: Feb. 8, 1990

Related U.S. Application Data

[63] Continuation-in-part of Ser. No. 222,527, Jul. 21, 1988, abandoned.

[51] Int. Cl.$^5$ ................ C07D 471/14; C07D 487/14; A61K 31/505

[52] U.S. Cl. .................................. 544/251; 548/375; 558/405

[58] Field of Search .......................................... 544/251

[56] References Cited

U.S. PATENT DOCUMENTS

| | | | |
|---|---|---|---|
| 4,075,210 | 2/1978 | Denzel et al. | 544/251 |
| 4,076,712 | 2/1978 | Denzel et al. | 544/251 |
| 4,261,996 | 4/1981 | Sircar et al. | 514/267 |
| 4,298,734 | 11/1981 | Temple . | |

FOREIGN PATENT DOCUMENTS

| | | | |
|---|---|---|---|
| 2150062 | 4/1973 | Fed. Rep. of Germany | 544/251 |
| 0001031 | 2/1990 | World Int. Prop. O. | 544/251 |

OTHER PUBLICATIONS

R. S. Long, "Chromium ... Acylacetonitriles" in *J. Am. Chem. Soc.*, 69 (1947), pp. 990–995.

P. L. Southwick et al., "The Condensation ... 2-Oxo-3-methoxy-3-pyrroline" in *J. Am. Chem. Soc.*, 75 (1953), pp. 3413–3417.

M. D. Reuber, "A Transplantable ... Rat" in *J. National Cancer Institute*, 26 (1961), pp. 891–897.

E. L. Anderson et al., "Synthesis ... 3-Amino-4-arylprazoles" in *J. Med. Chem.*, 7 (1964), pp. 259–268.

G. H. Rothblat, "Cholesteryl ... Hepatoma Cells" in *LIPIDS*, 9 (1974), pp. 526–535.

D. E. Brenneman et al., "Effect of dietary fat ... microsomes" in *J. of Lipid Research*, 18 (1977), pp. 582–591.

M. K. Jain et al., "Correlation ... Bilayer", in *Thrombosis Research*, 13 (1978), pp. 1067–1075).

E. B. Keeffe et al., "Alteration ... Metabolities" in *Gastroenterology*, 79 (1980), pp. 222–231.

T. Ogiso et al., "Fluidity ... Membrane" in *Biochimica et Biophysica Acta*, 649 (1981), pp. 325–335.

G. M. Doolittle et a., "Solubilization ... Cholesterol" in Biochemistry, 21 (1982), pp. 674–679.

F. P. Bell, "Effect of Chlorpromazine ... Synthesis" in *Experimental and Molecular Pathology*, 38 (1983), pp. 336–345.

G. Cighetti et al., "The Effect ... Animals" in *Life Sciences*, 33 (1983), pp. 2483–2488.

V. G. DeVries et a., "Potential ... Getaben" in *J. Med Chem.*, 26 (1983), pp. 1411–1421.

F. P. Bell, "Effects ... In Vitro" *J. of Cardiovascular Pharmacology*, 7 (1985), pp. 437–442.

K. E. Suckling et al., "Role ... metabolism" in *J. of Lipid Research*, 26 (1985), pp. 647–671.

V. G. DeVires et al., "Potential ... Activity" in *Comm. to the Editor, J. Med. Chem.*, 29 (1986), pp. 1131–1133.

F. P. Bell, "Arterial Cholesterol Esterification ... Inhibition by Drugs" in *Pharmacology Control of Hyperlipidaemia*, (1986), J. R. Prous, Science Publishers, pp. 409–422.

Illingworth, D. R., "Specific ... as hypocholesterolemic agents in humans, Mevinolin and Compactin" in *Pharmacological Control of Hyperlipidaemia*, J. R. Prous, Science Publishers (1986), pp. 231–249.

*Primary Examiner*—Mukund J. Shah
*Assistant Examiner*—L. Bernhardt
*Attorney, Agent, or Firm*—Gregory W. Steele; Sidney B. Williams, Jr.

[57] ABSTRACT

New pyrazolo-pyrrolo-pyrimidine-dione (PPPD) compounds of formula (I),

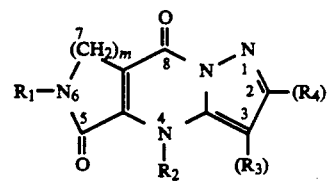

where $R_1$, $R_2$, $R_3$, $R_4$ and m are as defined in the specification, e.g., 4-(benzoylmethyl)-6-cyclohexyl-6,7-dihydro-2-phenyl-4H-pyrazolo[1,5-a]pyrrolo[3,4-d]pyrimidine-5,8-dione, have been found to be potentially useful to treat warm-blooded animal patients suffering from the symptoms of atherosclerosis and cholesterol buildup to relieve the same and for favorably altering the high density lipoprotein (HDL) to low density lipoprotein (LDL) ratio in blood samples of such patients.

16 Claims, No Drawings

PYRAZOLO-PYRROLO-PYRIMIDINE-DIONES

CROSS REFERENCE TO RELATED APPLICATIONS

This application is the national phase of international application PCT/US89/02854, filed Jul. 5, 1989, which is a continuation-in-part of Ser. No. 07/222,527, filed Jul. 21, 1988, now abandoned.

INTRODUCTION

This invention relates to new pyrazolo-pyrrolo-pyrimidine-dione (PPPD) derivatives as new compounds per se, and to their use as drugs to inhibit or control the ACAT (acyl CoA:cholesterol acyltransferase) enzyme to help a warm-blooded animal, including human patient to correct and regulate abnormal cholesterol metabolism rates in the animal cell system. More particularly, this invention provides some 2,4,6-trisubstituted-pyrazolo[1.5]-a[3,4-d]pyrimidine-5,8-dione (PPPD) derivative compounds per se, as active ingredients in pharmaceutical formulations to be used as anti-atherosclerotic drug medicines where the ACAT enzyme inhibition is desired, and to a method of using these new compounds as anti-atherosclerotic drug compounds in a valuable, warm-blooded animal patient including humans.

BACKGROUND OF THE INVENTION AND INFORMATION STATEMENT

Along with the HMG-CoA reductase (see Illingworth, D. R., "Specific . . . as hypocholesterolemic agents in humans", Mevinolin and Compactin" in *Pharmacological Control of Hyperlipidaemia*, J. R. Prous, Science Publishers (1986), pp. 231-249) and 7-alpha hydroxylase (see Cighetti, G. et al, "The effect . . . cholesterol 7-alpha hydroxylase . . . animals" in *Life Science*, 33 (1983), pp. 2483-2488) enzymes, acylCoA:-cholesterol acyltransferase (ACAT, EC 2.3.1.26), which latter enzyme is found in virtually all tissue but demonstrating highest activity in tissues such as the liver, intestine, adrenal and atherosclerotic arterial tissue, is known to be one of the major regulators of cholesterol metabolism in warm-blooded animal cells. Since the accumulation of esterified cholesterol is one of the characteristic features of atherosclerotic plaque (see Bell, F. P., "Arterial Cholesterol Esterification . . . Inhibition By Drugs", in *Pharmacological Control of Hyperlipidaemia* (1986), J. R. Prous, Science Publishers, pp. 409-422), the regulation of the ACAT enzyme activity is believed to be of significant importance in the treatment of atherosclerosis and related diseases in valuable animals including humans.

The ACAT enzyme is a constitutive protein in the endoplasmic reticulum and as such can be dramatically influenced by alterations in membrane fatty acid composition, phospholipid composition and cholesterol content (see Bell, F. P., supra; Doolittle, G. M. et al, "Solubilization . . . of AcylCoA:cholesterol Acyltransferase" in *Biochemistry*, 21 (1982), pp. 674-679, and Brenneman, D. E. et al, "Effects of Dietary Fat . . . Microsomes" *J. Lipid Research*, 18 (1977), pp. 583-591). It is recognized in the art that when such alteration or modifications in membrane fatty acid composition are extensive enough to alter membrane fluidity a number of cellular functions, which include among others, carrier-mediated transport, the properties of certain membrane-bound enzymes, binding to insulin and opiate receptors, etc., are affected.

An example of a known drug that has been shown to change the fluidity of membranes and is also an ACAT enzyme inhibitor is the tranquilizer, chlorpromazine (see Keefe, E. B. et al, "Alteration . . . By Chlorpromazine . . . ", *Gastroenterology*, 79, (1980), pp. 22-231; Ogiso, T. et al, "Fluidity . . . Chlorpromazine . . . Membrane", in *Biochim. Biophys. Acta*, 649 (1981), pp. 325-335 and Bell, F. P., "Effect of Chlorpromazine . . . Synthesis" in *Exp. Molec. Pathol.*, 38 (1983), pp. 336-346). Chlorpromazine is also known to have blood platelet aggregation inhibition properties (see Jain, M. K. et al, "Correlation of Inhibitors . . . Bilayer" in *Thrombosis Res.*, 13 (1978), pp. 1067-1075).

Other known drug compounds which also have ACAT enzyme inhibiting activity include the sedative-tranquilizer, diazepam, and the beta-blocker compound propanolol (see Bell, F. P., "Effects . . . Propanol . . . on ACAT Activity . . . Vitro", in *J. Cardiovasc. Pharmacol.*, 7 (1985), pp. 437-442).

6-Cyclohexyl-4,7-dihydro-2-phenyl-5H-pyrazolo[1,5-a]pyrrolo[3,4-d]pyrimidine-5,8(6H)-dione, utilized as a starting material to prepare compounds of this invention, was once commercially available. However, this compound is inactive in the ACAT enzyme screen.

Those in the art continue to search for new compounds which will be more potent as ACAT enzyme inhibitor compounds than known ACAT inhibitor drugs and/or drugs which will have no or fewer other drug property side effects.

OBJECTS OF THE INVENTION

It is an object of this invention to provide a group of pyrazolo pyrrolo-pyrimidine-dione and pyrazolo-pyrido-pyrimidine-dione derivative compounds (considered collectively herein as our PPPD derivative compounds) as new compounds per se.

It is another object of this invention to provide some pyrazolo-pyrrolo-(or pyridino)-pyrimidine-dione derivative compounds which are potentially useful as having useful ranges of ACAT enzyme inhibition properties so that they could be used as practical drug compounds for treating atherosclerotic disease conditions in a valuable, warm-blood animal, including human, patient.

It is another object of this invention to provide a method for treating a warm-blooded animal, including human, patient suffering the effects of an abnormal cholesterol buildup condition or from other atherosclerosis disease symptoms which involves administering to said patient one of the pyrazolo-pyrrolo-(or pyridino)-pyrimidine dione derivative compounds of this invention in an amount effective to alleviate the abnormal cholesterol buildup or athererosclerotic disease conditions or symptoms. Other objects, aspects and advantages of the invention will be apparent from the remaining specification which follows:

SUMMARY OF THE INVENTION

This invention provides new pyrazolo-pyrrolo-(or pyridino)-pyrimidine-dione derivative compounds of the formula I wherein $R_1$ is $C_4$ to $C_8$-cycloalkyl, $C_5$ to $C_{20}$-alkyl, $C_5$ to $C_{20}$-alkenyl, phenyl or phenyl-$C_1$ to $C_6$-alkyl;

$R_2$ is $C_1$ to $C_{20}$-alkyl, $C_5$ to $C_{20}$-alkenyl, phenylcarbonyl($C_1$ to $C_6$-alkyl)—, phenyl($C_1$ to $C_6$-alkyl), $C_1$ to $C_6$-alkyloxycarbonyl-$C_1$ to $C_6$-alkyl, (hydroxyimino)phenyl-($C_1$ to $C_6$-alkyl)—, (hydroxy)- phenyl($C_1$ to $C_6$-alkyl)—, or —$(CH_2)_n$-(phenyl)C=NOC(O)-G;

$R^3$ is hydrogen phenyl, or phenyl substituted with a halogen having an atomic number of from 9 to 35, hydroxy, $C_1$ to $C_6$-alkyl, $C_1$ to $C_6$-alkyloxy, or $C_2$ to $C_6$-alkenyl, $C_2$ to $C_6$-alkenyloxy;

$R_4$ is hydrogen, phenyl or phenyl substituted with a halogen having an atomic number of from 9 to 35, hydroxy, $C_1$ to $C_6$-alkyl, $C_1$ to $C_6$-alkyloxy, $C_2$ to $C_6$-alkenyl or $C_2$ to $C_6$-alkenyloxy, and G is $C_1$ to $C_{20}$-alkyl or $C_1$ to $C_{20}$-alkenyl;

m is 1 or 2;

n is 1 to 6; provided that when $R_3$ is a phenyl radical, $R_4$ is hydrogen, and when $R_4$ is other than hydrogen, $R_3$ is hydrogen. These compounds are lipophilic enough to penetrate the cell membrane. and the membrane of the endoplasmic reticulum which contain the ACAT enzyme.

This includes both the individual steroisomers and mixtures of stereoisomers of the compounds of Formula I.

This invention also includes a composition containing one of the formula I compounds in a pharmaceutical formulation, which composition in dosage unit form, is useful as a drug to correct and regulate abnormal cholesterol metabolism rates and for treating atherosclerosis conditions in a warm-blooded animal, including human, patient suffering from those conditions.

This invention also includes a method for treating a warm-blooded animal, including human, patient suffering the effects of an abnormal cholesterol building condition or from atherosclerosis disease symptoms which comprises administering to said patient one of the pyrazolo-pyrrolo-(or pyrido)-pyrimidine-dione derivative formula I compounds in an amount effective to reduce or alleviate the abnormal cholesterol buildup or other atherosclerotic disease condition or symptoms and to reduce blood plasma cholesterol levels by inhibiting sterol synthesis and/or blocking (inhibiting) the intestinal absorption of dietary and endogenous cholesterol in the body.

DETAILED DESCRIPTION OF THE INVENTION

Subgroups of the above formula I compounds which are preferred are, for example, (a) compounds of formula I wherein $R_1$ is $C_4$ to $C_8$-cycloalkyl, $R_2$ is phenyl($C_1$ to $C_3$-alkyl)—, or phenylcarbonyl($C_1$ to $C_3$-alkyl)— or —$(CH_2)_n$-phenyl)C=NOC(O)-G, $R_3$ is hydrogen, $R_4$ is selected from the group consisting of phenyl substituted, preferably in the 3- or 4-position, with $C_1$ to $C_4$-alkyl, $C_1$ to $C_4$-alkyloxy, or halogen having an atomic number of from 9 to 35, and m is 1, examples of which include:

6-cyclohexyl-6,7-dihydro-2-phenyl-4-(phenylmethyl)-4H-pyrazolo-[1,5-a]pyrrolo[3,4-d]dihydro-2-(4-ethoxyphenyl)-4-phenylmethyl-4H-pyrazolo[1,5-a]pyrrolo[3,4-d]pyrimidine-5,8-dione, 6-cyclohexyl-4-(phenylcarbonylmethyl)-2-(4-chlorophenyl)-6,7-dihydro-4H-pyrazolo[1,5-a]pyrrolo[3,4-d]pyrimidine-5,8-dione, and 6-cyclohexyl-6,7-dihydro-2-phenyl-4-(phenylcarbonylmethyl)-4H-pyrazolo[1,5-a]pyrrolo[3,4-d]pyrimidine-5-8-dione, (b) compounds of formula I wherein $R_1$ is phenyl or phenyl($C_1$ to $C_3$-alkyl)—

$R_2$ is phenyl($C_1$ to $C_3$-alkyl);

$R_3$ is hydrogen, $R_4$ is phenyl or phenyl substituted preferably in the 3- or 4-position with a $C_1$ to $C_4$-alkyl, $C_1$ to $C_4$-alkyloxy or a halogen having an atomic number of from 9 to 35, and m is 1, examples of which compounds include:

4,6-bis(phenylmethyl)-6,7-dihydro-2-phenyl-4H-pyrazolo[1,5-a]pyrrolo[3,4-d]pyrimidine-5,8-dione, (c) compounds of formula I wherein $R_1$ is $C_4$ to $C_8$-cycloalkyl, $R_2$ is phenyl($C_1$ to $C_3$-alkyl)—

$R_3$ is hydrogen, $R_4$ is selected from the group consisting of phenyl and phenyl substituted, preferably in the 3- or 4-position, with $C_1$ to $C_4$-alkyl, $C_1$ to $C_4$-alkyloxy, $C_2$ to $C_6$-alkenyl or $C_2$ to $C_6$alkenyloxy, and m is 2, examples of which compounds include:

6-cyclohexyl-2-phenyl-4-(phenylmethyl)-5,6,7,8-tetrahydro-4H-pyrazolo[1,5-a]pyrido[3,4-d]pyrimidine-5,8-dione, and (d) compounds of formula I wherein $R_1$ is $C_4$ to $C_8$-cycloalkyl, $R_2$ is a phenyl($C_1$ to $C_3$-alkyl)—

$R_3$ is selected from the group consisting of phenyl and phenyl substituted with $C_1$ to $C_4$-alkyl, $C_1$ to $C_4$-alkyloxy, hydroxy or halogen, and $R_4$ is hydrogen, and m is 1, an example of which is 6-cyclohexyl-6,7-dihydro-3-phenyl-4-(phenylmethyl)-4H-pyrazolo-[1,5-a]pyrrolo[3,4-d]pyrimidine-5,8-dione.

The carbon atom content of various hydrocarbon-containing moieties is indicated by a prefix designating the minimum and maximum number of carbon atoms in the moiety, i.e., the prefix ($C_i$-$C_j$) indicates a moiety of the integer "i" to the integer "j" carbon atoms, inclusive. Thus ($C_1$-$C_{20}$)alkyl refers to alkyl of one to twenty carbon atoms, inclusive, i.e., methyl, ethyl, propyl, butyl dodecyl and isomeric forms thereof. $C_5$-$C_{20}$ alkenyl indicates an alkenyl group containing five to twenty carbon atoms and one to three double bonds.

The compounds of this invention are useful for the prevention or treatment of atherosclerosis and related complications by, for example, lowering blood serum cholesterol or reduction of cholesterol in arterial tissue, possibly as a result of their ability to inhibit the enzyme acylCoA:cholesterol acyltransferase (ACAT). These compounds can be given neat but more probably would be given in combination with acceptable pharmaceutical diluent ingredients in appropriate dosage unit form such as tablets, capsules, ointments, sterile solutions and the like discussed more fully hereinbelow.

Additionally, the compounds of this invention have the potential to reduce plasma cholesterol levels by way of inhibition of sterol synthesis and/or blocking (inhibiting) the intestinal absorption of dietary and endogenous cholesterol in the body. These compounds also have the potential of being useful to treat inflammatory disorders at the dosage ranges indicated hereinbelow. We also believe that these new compounds, because of their possible mechanism of action in changing membrane fluidity may also be useful as local, topical anesthetic drugs, or useful as anti-arrhythmic, vasodilator, spasmolytic, muscle relaxant, anit-convulsant drugs or as modifiers of blood platelet functions, as sterol synthesis inhibitors and as inhibitors of sterol absorption in the animal intestine. These compounds may also function as calcium antagonist drugs since various known calcium channel blocker drugs such as nifedipine, diltiazem and verapamil also inhibit the ACAT enzyme.

Of the formula I compounds described and claimed as being within the scope of this invention, the compound 4-(benzoylmethyl)-6-cyclohexyl-6,7-dihydro-2-phenyl-4H-pyrazolo[1,5-a]pyrrolo[3,4-d]pyrimidine-5,8-dione, is considered to be the lead compound from this class of compounds that would be recommended for more advanced testing for use according to this invention. The "4-(benzoylmethyl)" group can also be named —4-(phenylcarbonylmethyl)—.

The compounds of this invention in general can be prepared by known chemical procedures involving reaction of the selected alkylating agent $R_2$-X where $R_2$ is as defined above and X is a halogen, preferably a chlorine or bromine, or an epoxide derivative, or other reactive form of an $R_2$-X compound with the 4-(N-non-substituted)-6-($R_1$)-2-($R_4$)-3-($R_3$)-pyrazolo[1,5-a]pyrrolo[3,4-d]pyrimidine-5,8-dione (PPPD) ring structure compound under N-alkylating conditions, which usually include mixing the $R_2$-X reactant and the PPPD compound (VI) in an organic solvent for the mixture in the presence of a base such as an alkali metal carbonate, e.g., potassium carbonate, at room temperature or at moderately elevated temperatures, e.g., to 40° C. to 100° C. for a time sufficient to effect as complete a reaction as possible, e.g., from two to 48 hours, depending upon the choice of reactants, the selected solvent, the size of the batch, the degree of completion of the reaction and other factors of concern to the chemist monitoring the reaction.

The resulting reaction mixture can then be treated by conventional chemical processing procedures, e.g., by dilution, filtration, concentration and cooling procedures to separate the formula I product compound from reactants, base and initial solvent materials. The products of this invention are generally high melting crystalline solids, most of them melting over 180° C., which are easily separated by filtration or centrifugation procedures, and they can be recrystallized from conventional liquid hydrocarbon or liquid hydrocarbon/polar liquid solvent mixtures upon heating, to effect solution of the formula I compound therein, and then crystallized by cooling the solution to effect precipitation of the more pure formula I compound.

At least one PPPD compound, that of Preparation I hereinbelow, was commercially available for a time, but now it does not seem to be commercially available. In such a case the starting PPPD compound has to be prepared by chemical process procedures. Such a process is outlined with chemical formulas herebelow where starting with the selected alpha-cyano-ketone or aldehyde, $R_4$—C(O)—C($R_3$)—CN (II), is reacted with hydrazine, $H_2N.NH_2$ (III), preferably in the form of hydrazine monohydrate, as shown, (which is less explosive to handle) in the presence of a base such as alkali metal alkoxide, e.g., sodium ethoxide, and an organic diluent or solvent such as toluene to form the selected 3-amino-4-($R_3$)-5-($R_4$)-pyrazole intermediate reactant compound (IV).

The selected 3-amino-pyrazole reactant (IV) is then reacted with a selected pyrrolidinecarboxylate ester (V), such as $C_1$ to $C_6$-alkyl 1-($R_1$)-4,5-dioxo-3-pyrrolidinecarboxylate ester, e.g., ethyl 1-cyclohexyl-4,5-dioxo-3-pyrrolidinecarboxylate in an acidic medium such as glacial acetic acid, or the like, while heating the mixture often to reflux temperature of the mixtures to speed up the rate of reaction to form the PPPD precursor compound, 2-($R_4$)-3-($R_3$)-(H)-6-($R_1$) pyrazolo-[1.5-a]pyrrolo (or pyrido)[3,4-d]pyrimidine-5,8-dione (VI), which can be purified if desired or used directly as a crude product as a reactant with the alkylating form of the $R_2$-X reactant, as indicated above, to form the compounds of this invention (I). The desired compound (I) can be recovered from its reaction mixture by dilution of the reaction mixture with water followed by collection of the insoluble solid (compound I) by filtration or extraction with a solvent. The impure product (I) is placed into an appropriate pure or mixed solvent system, e.g., chloroform/ethanol, and similar type mixture, heating to effect solution of the compound (I) followed by cooling the mixture to precipitate a more pure crystalline form of the desired compound (I).

Methods for preparing the compounds which are the active drug compounds for use according to the invention are further exemplified by the following detailed examples.

For brevity, some of these examples use common shorthand chemical terms. Temperatures are in degrees Celsius, unless otherwise indicated. The letter h. means hours. The term 1H NMR ($CDCl_3$, δ) means proton nuclear magnetic resonance spectral analysis in delta scale units. IR means infrared spectral analysis, UV mean ultraviolet spectral analysis. HCl means hydrogen chloride, often in aqueous (aq). solution. DMSO means dimethylsulfoxide as a solvent or as a solvent for NMR spectral analysis. TLC means thin layer chromatography analysis. DMF means N,N-dimethylformamide, a common laboratory solvent.

PREPARATION 1

6-Cyclohexyl-4,7-dihydro-2-phenyl-5H-pyrazolo[1,5-a]pyrrolo[3,4-d]pyrimidine-5,8(6H)-dione

A. Benzoyl acetonitrile

To a suspension of sodium ethoxide (34.0 g. 0.500 mole) in dry toluene (200 mL were added ethyl benzoate (71.4 mL, 0.500 mole) and dry acetonitrile (32 mL, 0.60 mole). The mixture was mechanically stirred under nitrogen at 105°–110° C. for 29 hours, during which time it became quite viscous. After cooling to room temperature, water (300 mL) was added and the mixture was washed with ethyl ether (2×100 mL). The aqueous layer was then acidified to pH 5–6 with con. aq. HCl (required 30–35 mL) and the resulting crystalline precipitate was collected by suction filtration, washed twice with water, and air-dried. This subtitled material (49.23 g, 68%, m.p. 72°–73°) was sufficiently pure to be used in further transformations (lit., m.p. 80°–81°, Long, R. S., *J. Am. Chem. Soc.*, (1947), 69, p. 990. [1]NMR ($CDCl_3$, δ) 7.95 (dd, 2H, J=7, 2 Hz, o-aryl), 7.6 (m, 3H, aryl), 4.1 (s, 2H, $CH_2$). This benzoyl acetonitrile intermediate is also now commercially available but we prepared ours as above.

B. 3-Amino-5-phenylpyrazole

Benzoyl acetonitrile from part A hereinabove (10.0 g, 68.9 mmole) and hydrazine monohydrate (4.34 mL, 89.6 mmole) were combined in 95% ethanol (90 mL) and refluxed for 1.5 hours. The solvent was evaporated under vacuum and the crystalline subtitled compound, residue was crystallized from chloroform (three crops, 9.49 g, 86%, m.p. 125°–126.5°, lit., m.p. 123°–125°, Taylor, E. C. et al., *J. Org. Chem.*, (1966), 31, page 1818.

C.

6-Cyclohexyl-4,7-dihydro-2-phenyl-5H-pyrazolo(1,5-a)—pyrrolo-(3,4-d)pyridimidine-5,8(6H)-dione The 3-amino-5-phenylpyrazole from part B hereinabove (6.85 g, 43.0 mmole) and ethyl 1-cyclohexyl,4-5-dioxo-3,pyrrolidinecarboxylate [Southwich, P. L. et al., *J. Am. Chem. Soc.*, (1953), 75, page 3413] (10.90 g, 43.0 mmole) were combined in glacial acetic acid (45 mL) and stirred at reflux for five hours, during which time a copious precipitate of the insoluble product appeared. After cooling to room temperature, the reaction was diluted with absolute ethanol (200 mL) and stirred for 20 minutes. The microcrystalline precipitate was collected by suction filtration and washed twice with more ethanol. Drying under vacuum afforded a pale yellow finely crystalline solid (10.94 g, 73%, m.p. >320) which was pure as judged by NMR and elemental analysis. The proton NMR was identical to a sample purchased from Maybridge Chemical Company (KM 418). $^1$H NMR (DMSO d6, δ) 8.0 (dd, 2H, J=8,2 HZ, o-aryl), 7.45 (m, 3H, m and p aryl), 6.67 (s, 1H, pyrazole-H), 4.39 (bs, 2H, lactam CH$_2$), 3.98 (m, 1H, cyclohexyl CH), 1.1–1.9 (m, 10H); IR (mull) 1693, 1671, 1633, 1622, 1463 cm$^{-1}$; IV (EtOH) λ max (ε) 206 (27,030), 229 (24,860), 252 (26,760), 270 (36,220), 280 sh. (27,440), 300 sh. (8,300), 317 sh. (5,650), 343 (5,470); MS m/e (rel. intent.) 349 (25), 348 (M+, 100), 305 (14), 267 (14), 266 (66); calc'd mass for C$_{20}$H$_{20}$N$_4$O$_2$ =348.1586, found =348.1569; Anal. cal'd =C, 68.95; H, 5.79; N; 16.08; found =C, 68.62; H, 5.81; N, 15.94; TLC (silica, 2/1 CHCl$_3$/EtOAc) Rf 0.33 (streaked).

EXAMPLE 1

6-Cyclohexyl-4-(5-hexenyl)-6,7-dihydro-2-phenyl-4H-pyrazolo[1,5-a]pyrrolo[3,4-d]pyrimidine-5,8-dione The pyrazole derivative compound from Preparation 1 hereinabove (3.76 g, 10.8 mmol), 6-bromo-I-hexene (2.89) ml, 21.5 mmole) and potassium carbonate (1.49 g, 10.8 mmole) were stirred in N,N-di-methylformamide (DMF) (54 ml) at 60°–65° C. for 24 hours. The resulting red mixture was partitioned between water (150 ml) and ethyl acetate (150 mL). The organic layers were washed with water (3×45 ml, 1×90 ml), dried with magnesium sulfate and concentrated to produce an orange solid. The solid was dissolved in boiling hexane/ethyl acetate (2/1, 300 mL) and filtered while hot to remove undissolved solid. Cooling to 0° C. afforded the titled compound 4.33 g of pale yellow plates (93%, m.p. 144.5–146).

$^1$H NMR CDCl$_3$, δ) 8.05 (m, 2H, o-phenyl-H), 7.45 (m, 3H, m,p-phenyl-H), 6.48 (s, 1H, pyrazole-H), 5.7 (ddt, 1H, J=17, 10, 6 Hz, vinyl CH), 5.04 (dm, 1H, J=17 Hz, vinyl CH$_2$), 5.0 (dm, 1H, H, J=10 Hz, vinyl CH$_2$), 4.67 (t, 2H, J=7 Hz, 4-NCH$_2$), 4.35 (s, 2H, lactam CH$_2$), 4.14 (m, 1H, cyclohexyl CH), 2.15 (q, 2H, H=7 Hz, allyl CH$_2$), 1.1–2.0 (m, 14H); IR (mull, cm$^{-1}$) 1698, 1689, 1622, 1588, 1574, 1461, 1452; UV (ethanol) λ max(ε) 206 (25,670), 228 (24,600), 269 (33,000), 285sh (16,000), 295sh (10,430), 340 (6,140); MS m/e (rel. intens.) 430 (M+, 1), 335 (7), 290 (3), 248 (72), 156 (100); Analysis calc'd for C$_{26}$H$_{30}$N$_4$O$_2$ =C, 72.53; H, 7.02; N, 13.01; Found=C, 72,36; H, 7.25; N, 12.74; TLC (silica, 35% ethyl acetate/-hexane) Rf 0.27.

EXAMPLE 2

6-Cyclohexyl-6,7-dihydro-2-phenyl-4-(phenylmethyl)-4H-pyrazolo[1,5-a]pyrrolo[3,4-d]pyrimidine-5,8-dione To a suspension of 6-cyclohexyl-4,7-dihydro-2-phenyl-5H-pyrazolo[1,5-a]pyrrolo[3,4-d]pyrimidine-5,8(6H)-dione, prepared as described in Preparation 1 hereinabove, (2.00 g., 5.74 mmoles) and anhydrous potassium carbonate (795 mg., 5.75 mmole) in dry DMF (30 ml. in a flask there was added benzyl bromide (1.37 ml., 11.5 mmoles). The flask was stoppered tightly and stirred at room temperature for 24 hours. The mixture was diluted with water (150 ml.), stirred for 30 minutes and suction filtered. The collected solid was washed twice more water and air dried. The resulting solid was crystallized from an ethanol/chloroform, about 3/1 V/V ratio, 650 ml., dissolved at reflux temperature of the mixture and then cooled to 0° C. to afford 2.11 g. of the tilted product as fine, ivory colored needle crystals (84% yield,, m.p. 276°–278° C.). $^1$H NMR (CDCl$_3$) 8.0 (m,2H, pyrazole o-phenyl), 7.3–7.5 (m,8H, phenyl), 6.44 (s, 1H, pyrazole-H), 5.93 (s, 2H, CH$_2$phenyl), 4.41 (s, 2H, lactam CH$_2$), 4.18 (m, 1H, cyclohexyl CH), 1.1–2.0 (m, 10H, cyclohexyl CH$_2$); IR (mull, cm$^1$) 1697, 1679, 1618, 1591, 1577; UV (ethanol) λ max (ε)205(35,680), 227(23,860), 267(33,080), 285 sh (15,450), 295 sh (11,460) 338 (6,870); MS m/e (rel. intens.) 438(M+,15), 347(5), 91(100); Anal. calcd. for C$_{27}$H$_{26}$N$_4$O$_2$: % Calcd.: C, 73.95; H, 5.98; N, 12.78; % Found: C, 73.88; H, 6.07; N, 12.80. TLC (silica, 4/1 V/V chloroform/ethylacetate) Rf 0.56.

EXAMPLE 3

6-Cyclohexyl-6,7-dihydro-4-hexyl-2-phenyl-4H-pyrazolo[1,5-a]pyrrolo[3,4-d]pyrimidine-5,8-dione A suspension of the prazole derivative compound from Preparation 1 hereinabove (2.00 g, 5.74 mmole), 1-iodohexane (1.7 mL, 12 mmole), and anhydrous potassium carbonate (800 mg. 5.8 mmole) in dry DMF (30 mL) was stirred in a stoppered flask at room temperature for 26 hours. The mixture was diluted with water (150 mL), stirred for 15 minutes and suction filtered. The collected solid was washed with water and air-dried. Separation from residual starting pyrazole derivative was achieved by dissolving the crude solid in chloroform (100mL) and filtering through a medium glass frit. Concentration of the filtrate under vacuum left a solid which was crystallized from 95% ethanol (100 mL, reflux to 0° C.) to afford 0.92 g (37% ) of the titled compound as white needles (m.p. 162°–164°). $^1$H (CDCl$_3$, δ) 8.04 (dd, 2H, J=2, 8 Hz, phenyl-H(ortho)), 7.45 (m, 3H, phenyl-H (meta, para), 6.48 (s, 1H, pyrazole-H), 4.65 (t, 2H, J=7 HZ, 4-N-CH$_2$), 4.36 (s, 2H, lactam CH$_2$) 4.15 (m, 1H, cyclohexyl CH), 1.1–2.0 (m, 18H, CH$_2$), 0.89 (t, 3H, CH$_3$); IR (mull, cm$^{-1}$) 1700, 1687, 1627, 1616, 1589, 1575, 1454; (UV (ethanol) λmax (ε) 206 (25,430), 228 (24,310), 268 (32,700), 295sh (10,250), 342(6,230); MS m/e (rel. intens.) 433 (M+1, 30), 432 (M+, 100) 362(12), 348(44), 267(46), 266(51), 265(78); Analysis calc'd for C$_{26}$H$_{32}$N$_4$O$_2$=C, 72.19; H, 7.46; N, 12.95; Found=C, 71.88; H, 7.46; N, 12.77; TLC (silica 2/1 chloroform/ethyl acetate) Rf 0.84.

EXAMPLE 4

4-(Benzoylmethyl)-6-cyclohexyl-6,7-dihydro-2-phenyl-4H-pyrazolo[1,5-a]pyrrolo-[3,4-d]pyrimidine-5,8-dione A (2.00 g, 5.74 mmole) portion of the pyrazole derivative compound from Preparation 1 hereinabove, chloroacetophenone (1.77 g, 11.5 mmole), and anhydrous potassium carbonate (830 mg., 6.0 mmole) were combined in dry DMF (30 mL) and stirred at room temperature in a stoppered flask for 24 hours. Water (150 mL) was added and the mixture was stirred for 15 minutes before suction filtration. The lumpy solid collected was washed with more water, air dried and crystallized from 95% ethanol (150 mL, reflux to 0°) to afford 1.33 g. of the titled compound as a pale yellow microcrystalline solid. A second recrystallization provided 1.22 g (m.p. 164°-167° (42%). $^1$H NMR (CDCl$_3$, δ) 8.05 (d, 2H, J=9 Hz, CO(o-phenyl-H)), 7.95 (m, 2H, pyrazole(o-phenyl-H)), 7.67 (t, 1H, J=8 Hz, CO(p-phenyl-H)), 7.45 (t, 2H, J=8 Hz, CO(m-methyl-H)), 7.40 (m, 3H, pyrazole(m,p-phenyl)), 6.27 (s, 1H, pyrazole-H), 6.08 (bs, 2H, NCH$_2$CO), 4.36 (s, 2H, lactam (CH$_2$), 4.03 (m, 1H, cyclohexyl CH), 1.1–1.9 (m, 10H, cyclohexyl CH$_2$); IR (mull, cm$^{-1}$), 1691, 1633, 1620, 1593, 1578, 1463, 1449; UV (ethanol) λmax(ε) 204 (42,800), 230sh (27,200), 246(37,860), 262(33,720), 285(16,700), 293(12,560), 335(7,000), MS m/e (rel. intens.) 467 (M+1, 17), 466(M$^{30}$, 53), 361 (28), 347 (5), 249 (12), 105 (100); Exact mass calc'd for C$_{28}$H$_{26}$N$_4$O$_3$=466.2005; Found=466.2004; Analysis calc'd=C, 72.09; H, 5.62; N, 12.01; Found=C, 71.08; H, 5.59; N, 11.86; TLC (silica, 1/1 chloroform/ethyl acetate) Rf 0.71.

EXAMPLE 5

6-Cyclohexyl-6,7-dihydro-4-methyl-2-phenyl-4H-pyrazolo-[1,5-a]pyrrolo[3,4-d]pyrimidine-5,8-dione To a suspension of 6-cyclohexyl-4,7-dihydro-2-phenyl-5H-pyrazolo[1,5-a]pyrrolo[3,4-d]pyrimidine-5,8(6H)dione (2.00 g, 5.75 mmole) and potassium carbonate (795 mg, 5.75 mmole) in dry dimethylformamide (DMF, 30 mL) was added methyl iodide (0.72 mL, 12 mmole). The flask was stoppered tightly and stirred at room temperature for 24 hours. The mixture was diluted with water (150 mL), stirred for 10 minutes and suction filtered. The collected solid was washed once with water and once with 95% ethanol. Drying under vacuum left 1.91 g of white powdery solid. Crystallization from 95% ethanol (500 mL) afforded the titled product as fine white needles (1.73 g, 83%, m.p. 276°-279°). $^1$H NMR (CDCl$_3$, δ) 8.05 (m, 2H, 2-phenyl H), 7.45 (m, 3H, 3,4-phenyl H), 6.45 (s, 1H, pyrazole-H), 4.33 (s, 2H, lactam CH$_2$), 4.16 (s, 3H, CH$_3$), 4.15 (m, 1H, cyclohexyl CH), 1.1–2.0 (m, 10H, cyclohexyl CH$_2$); IR (mull, cm$^{-1}$) 1693, 1627, 1590, 1574; UV (ethanol) λmax (ε) 206 (27,300), 226(23,920), 268(33,740), 285sh(15,570), 295(10,940), 338(6,090); MS m/e (rel. intens.) 363 (M+1, 25) 362 (M+, 100), 319(35), 280(66); Analysis calc'd for C$_{21}$H$_{22}$N$_4$O$_2$=C, 65,59; H, 6.12 N, 15.46; Found=C, 69.64; H, 6.21; N, 15.43. TLC (silica, ethylacetate) Rf 0.80.

EXAMPLE 6

6-Cyclohexyl-6,7-dihydro-2-(4-ethoxyphenyl)-4-(phenylmethyl)-(4H)-pyrazolo[1,5-a]pyrrolo[3,4-d]pyrimidine-5,8-dione

A. p-Ethoxybenzoyl acetonitrile

Ethyl 4-ethoxybenzoate (45.3 mL, 250 mmole) was added to a suspension of sodium ethoxide (17.0 g, 250 mmole) and acetonitrile (16 mL, 300 mmole) in dry toluene (100 mL) and the mixture was mechanically stirred at 106°-110° for 26 hours. The reaction was then cooled and diluted with water (400 mL). After most of the solid had dissolved, the solution was washed with ethyl ether (2×200 mL) and then acidified with concentrated HCl (approximately 20 mL) to pH of about 5. The copious off-white precipitate was collected by suction filtration and air dried. Crystallization from 95% ethanol (350 mL) provided 21.3 g. of the subtitled compound as white needles, sufficiently pure for further transformation (yield: 45%). $^1$H NMR (CDCl$_3$, δ) 7.85 (d, 2H, J=8 Hz, o-phenyl), 6.95 (d, 2H, J=8 Hz, m-phenyl), 4.1 (q, 2H, J=7 Hz, OCH$_2$), 4.0 (s, 2H, CH$_2$CN), 1.45 (t, 3H, CH$_3$).

B. 5-(4-Ethoxyphenyl)pyrazol-3-amine

A (21.1 g, 112 mmole) portion of p-ethoxy-benzoylacetonitrile from Part A hereinabove and hydrazine monohydrate (7.0 mL, 144 mmole) were combined in 95% ethanol (145 mL) and refluxed for two hours. After cooling, the solvent was evaporated under vacuum and the crystalline residue recrystallized from ethyl acetate (500 mL) to afford 16.14 g (71%) of the subtitled compound as fine white needles (m.p. 152°-156°). An analytical sample was prepared with a second recrystallization (m.p. 155°-157°). $^1$H NMR (DMSO d6, δ) 7.57 (d, 2H, J=9 Hz, o-phenyl), 6.93 (d, 2H, J=9 Hz, m-phenyl), 5.70 (bs, 1H, pyrazole N-H), 4.35 (bs, 2H, NH$_2$), 4.03 (q, 2H, J=7 Hz), 1.34 (t, 3H, J=7 Hz); IR (mull) 3397, 3136, 1615; 1519, 1474 cm$^{-1}$; UV (ethanol) λ-max(ε) 205(25000), 261(20500); MS m/e(rel. intens.) 203 (M+, 100), 175, (90), 146 (35); Analysis calc'd for C$_{11}$H$_{13}$N$_3$O=C, 65.01; H, 6.45; N, 20.67; found=C, 64.73; H, 6.77; N, 20.59; TLC (silica, 15% MeOH/CHCl$_3$) Rf=0.50.

C.

6-Cyclohexyl-2-(4-ethoxyphenyl)-4,7-dihydro-5H-pyrazolo[1,5-a]pyrrolo[3,4-d]pyrimidine-5,8-dione A 3.05 g, 15.0 mmole portion of the 5-(4-ethoxyphenyl)pyrazol-3-amine from part B hereinabove and ethyl 1-cyclohexyl-4,5-dioxo-3-pyrrolidinecarboxylate ester (3.80 g, 15.0 mmole) were combined in glacial acetic acid (15 mL) and refluxed for four hours. After cooling, the reaction was diluted with 95% ethanol (120 mL), stirred for 15 minutes and suction filtered. The pale yellow crystalline solid collected was washed twice with more ethanol and dried under vacuum, affording 4.78 g (81%) of the subtitled compound, pure as judged by elemental analysis (m.p. 310°). $^1$H NMR (DMSO d6,δ) 7.95 (d, 2H, J=8 Hz, 2-phenyl H), 7.04 (d, J=8 Hz, 3-phenyl H), 4.40 (bs, 2H, lactam CH$_2$), 4.11 (q, 2H, J=7 HZ, OCH$_2$), 4.0 (m, 1H, cyclohexyl CH), 1.38 (t, 3H, J=7 Hz), 1.3–1.9 (m, 10H); IR (mull) 1694, 1675, 1641, 1615 cm$^{-1}$; UV (ethanol) λmax(ε) 208 (28260), 226 (24100), 276 (38000), 285 (32950), 345 (6230); MS m/e (rel. intens.) 393 (26), 393 (M+, 100), 310 (27), 282 (37); Analysis calc'd for C$_{22}$H$_{24}$N$_4$O$_3$=C, 67.33; H, 6.16; N. 14.28; found=C, 67.37; H, 6.22; N, 14.26.

D.

6-Cyclohexyl-6,7-dihydro-2-(4-ethoxyphenyl)-4-phenylmethyl)-4H-pyrazolo[1,5-a]pyrrolo[3,4-d]pyridimine-5,8-dione A suspension of the pyrazolo-pyrrolo-pyrimidine-5,8(6H)dione from part C hereinabove (1.98 g, 5.05 mmole), potassium carbonate (720 mg, 5.2 mmole), and benzyl bromide (1.2 mL, 10 mmole) in dry DMF (27 mL) was stirred in a stoppered flask at room temperature for 24 hours. The mixture was diluted with water (150 mL), stirred for 10 minutes and suction filtered. The yellow solid collecetd was washed with water and air dried. The crude material was crystallized by suspending in boiling ethanol (300 mL) and adding chloroform (50 mL) until complete dissolution occurred. Cooling to 0° C. afforded 2.18 g (89%) of the titled compound product as a pale yellow microcrystalline solid (m.p. 263°-266°). Exposure to high vacuum at 75° C. was necessary to remove all residual ethanol land obtain a satisfactory elemental analysis. $^1$H NMR (CDCl$_3$) 7.9 (d, 2H, J=9 Hz, 2-phenyl-H (ortho)), 7.35 (m, 5H, phenyl), 6.94 (d, 2H, J=9 Hz, 2-phenyl-H(meta)), 6.35 (s, 1H, pyrazole-H), 5.91 (s, 2H, benzyl CH$_2$), 4.38 (s, 2H, lactam CH$_2$), 4.15 (m, 1H, cyclohexyl CH$_2$), 4.09 (q, 2H, J=7 Hz, OCH$_2$), 1.45 (t, 3H, J=7 Hz, CH$_3$), 1.1–2.0 (m, 10H, cyclohexyl CH$_2$); IR (mull, cm$^{-1}$) 1684, 1681, 1617, 1592, 1452, 1253; UV (ethanol) λmax(ε) 206(30,400), 225(23,400), 272(29,700), 295sh(14,500), 308(14,100); MS m/e rel. intens.) 483 (M+1, 51), 482 (M+, 100), 391 (18), 309 (23), 118 (14), 91 (100); Analysis calc'd for C$_{29}$H$_{30}$N$_4$O$_3$ =C, 72.18; H, 6.27; N, 11.61; Found =C, 71.76; H, 6.43; N, 11.63; TLC (silica, ethyl acetate) Rf 0.75

EXAMPLE 7

6,7-Dihydro-2,6-diphenyl-4-(phenylmethyl-4H-pyrazolo[1.5-a]pyrrp;p[3,4-d]pyrimidine-5,8-dione A. 4,5-Dioxo-1-phenylpyrrolidine-3-carboxylic acid, ethyl ester To a solution of the β-amino ester ethyl 3-anilinopropoxylate (Southwick, P.L. et al., *J. Am. Chem. Soc.*, (1949), 71, page 2532) (23.0 g, 0.119 mole) in absolute ethanol (40 mL) were added diethyl oxalate (16.2 mL, 0.119 mole) and a solution of sodium ethoxide in ethanol (21 wt%, 44.4 mL, 0.12 mole). The reaction solidified within a few minutes at room temperature. The solid mass was then heated on a steam bath under a reflux condenser for one hour. Removal of the solvlent under vacuum followed after cooling. The solid residue was dissolved in 400 mL of boiling water. While stirring vigorously, the solution was acidified with concentrated HCl (9 mL) and stirring continued for one hour before cooling in an ice bath. The crystalline solid was collected by suction filtration and crystallized from 95% ethanol (170 mL) to afford 16.37 g (56%) of light tan needles (m.p. 153°–155°, lit. (southwick, P.C. et al, *J. Am. Chem. Soc.*, (1953), 75, page 3413) m.p. 153°). A second crop provided 2.96 g for a total of 19.35 g (66%). $^1$H NMR (DMSO d6, δ) 7.84 (d, 2H, J=9 Hz, o-phenyl), 7.43 (t, 2H, J=9 Hz, m phenyl), 7.19 (t, 1H, J=9 Hz, p-phenyl), 4.48 (s, 2H, NCH$_2$), 4.21 (q, 2H, J=7 Hz, OCH$_2$), 1.27 (t, 3H, J=7 HZ); IR (mull) 3550, 1719, 1690, 1663 cm$^{-1}$; MS m/e (rel. intens.) 247(M+, 91), 201(42), 119(57), 105(73), 82(100); Anal. Calc'd for C$_{13}$H$_{13}$NO$_4$ =C, 63.15; H, 5.30; N, 5.66; Found =C, 62.92; H, 5.29; N, 5.56.

B.

4,7-Dihydro-2,6-diphenyl-5H,pyrazolo[(1,5-a)]pyrrolo[(3,4-d])pyrimidine-5,8(6H)-dione The ethyl 4,5-dioxo-1-phenylpyrrolidine-3-carboxylate ester, from Part A hereinabove, (4.95 g, 20.0 mmole) and the 3-amino-5-phenylpyrazole frome Preparation 1, Part B hereinabove (3.18 g, 20.0 mmole) were combined in glacial acetic acid (20 mL) and refluxed for 3 hours. The thick pale yellow slurry was cooled and diluted with ethanol (150 ml) and stirred for one hour before collecting the solid by suction filtration. After washing twice with more ethanol, the solid was dried under vacuum, leaving 5.35 g of the subtitled compound as a powdery solid (m.p.>320°) (78%). An analytical sample was obtained by recrystallization of 3.15 g from DMSO (400 mL, 150° to 25°) to afford 2.58 g of cream microcrystalline solid. $^1$H NMR (DMSO d6, δ) 8.05 (d, 2H, J=8 Hz, o-phenyl(pyrazole)), 7.96 (d, 2H, J =8 Hz, o-phenyl(lactam)), 7.5 (m, 5H, phenyl), 7.29 (t, 1H, J=8 Hz, p-phenyl(lactam)), 6.75 (s, 1H, pyrazole-H), 4.98 (bs, 2H, lactam CH$_2$); IR (mull) 1700, 1678, 1645, 1609 cm$^{-1}$; UV (ethanol) λmax(ε) 205 (20240), 231 (15550), 247 (17050), 278 (21160), 285 (22350), 365 (3780); MS m/e (rel. intens.) 343(23), 343(M+, 100), 313(15), 285(20), 185(20), 77(48); Analysis calc'd for C$_{20}$H$_{14}$N$_4$O$_2$ =C, 70.17; H, 4.12; N, 16.36; found =C, 70.10; H, 4.22; N, 16.29

C.

6,7-Dihydro-2,6-diphenyl-4-(phenylmethyl)-4H-pyrazolo[1,5-a]pyrrolo[3,4-d]-pyrimidine-5,8-dione The 4-position N-unsubstituted-dione compound from part B hereinabove (1.75 g, 5.11 mmole), benzyl bromide (1.2 mL, 10.2 mmole) and potassium carbonate (720 mg, 5.2 mmole) in dry DMF (27 mL) were stirred in a capped flask at room temperature for 24 hours. The reaction was diluted with water (150 mL), stirred for ten minutes and suction filtered. The collected solid was washed with more water and air dried. The crude solid was crystallized from 1/1 chloroform/-ethanol (400 mL, reflux to 0° C.) to afford 2.30 g of cream fine needles. Unsatisfactory elemental analysis prompted recrystallization from chloroform (100 mL, reflux to 0° C.), affording 1.76 g (80%)(m.p. 271°-272° C.) of the titled compound. $^1$H NMR (CDCL$_3$, δ) 7.99 (dd, 2H, J=2, 8 Hz, 2-phenyl-H (orthol)), 7.81 (bd, 2H, J=8 Hz, 6-phenyl-H (orthol)), 7.3 –7.6 (m, 11H, phenyl-H), 6.49 (s, 1H, pyrazole-H), 5.99 (s, 2H, NCH$_2$Ph), 4.90 (s, 2H, lactam CH$_2$); IR (mull, cm$^{-1}$) 1706, 1692, 1685, 1632, 1592, 1577; UV (ethanol) λmax(ε) 227 (25,350), 270 (24,460), 286sh (13,240), 315 (12,900), 330sh (11,500); MS m/e (rel. intens.) 433 (M+1, 43), 432.(M+, 100), 355 (9), 341 (17), 328 (100), 102 (20), 91 (100), 77 (27); Exact mass calc'd for C$_{27}$H$_{20}$N$_4$O$_2$ =432.1586; Found =432.1589; TLC (silica, ethyl acetate) Rf 0.88.

EXAMPLE 8

4,6-Bis(phenylmethyl)-6,7-dihydro-2-phenyl-4H-pyrazolo-[1,5a]pyrrolo[3,4-d]pyrimidine-5,8-dione

A.

6-Benzyl-4,7-dihydro-2-phenyl-5H-pyrazolo(1,5-a)pyrrolo(3,4-d)pyrimidine-5,8(6H)-dione The aminoopyrazole, 5-phenylpyrazol-3-amine (3.18 g, 20.0 mmole) and ethyl 1-(phenylmethyl)-4,5-dioxo-3- pyrrolidinecarboxylate ester (5.22 g, 20,0 mmole) were refluxed in glacial acetic acid (20 mL) for five hours. After cooling, the reaction was diluted with 95% ethanol (120 mL) and stirred to 10 minutes. The microcrystalline precipitate was collected by suction filtration and washed twice with more ethanol. Drying under vacuum left 4.65 g (65%) of pale yellow microcrystalline solid which was pure as judged by elemental analysis (m.p. >320). $^1$H NMR (DMSO d6,δ) 8.01 (dd, 2H, J=8, 2 Hz, o-phenyl on pyrazole), 7.3–7.6 (m, 8H, aryl), 6.70 (s, 1H, pyrazole-H), 4.78 (bs, 2H, $CH_2$Ph), 4.32 (bs, 2H, lactam $CH_2$); IR (mull) 1697, 1678, 1633, 1606 cm$^{-1}$; MS m/e (rel. intens.) 357(15), 356(M+, 59), 265(4); 223(4), 106(12), 91(100); Anal. calc'd for $C_{21}H_{16}N_4O_2$=C, 70.77; H, 4.53; N, 15.72; found=C, 70.43; H, 4.66; N, 15.37; TLC (silica, ethyl acetate) Rf 0.63 (streaked).

B.
4,6-Bis(phenylmethyl)-6,7-dihydro-2-phenyl-4H-pyrazolo[1,5-a]pyrrolo[3,4-d]pyrimidine-5,8-dione A suspension of the 6-benzyl-dione compound from part A hereinabove (2.08 g, 5.84 nmole), benzyl bromide (1.4 mL), 12 mmole) and anhydrous potassium carbonate (830 mg. 6.0 mmole) in dry DMF (30 mL) was stirred in a stoppered flask at room temperature for 24 hours. The mixture was diluted with water (150 mL) and extracted with chloroform (2×70 mL). The organic extracts were combined and washed with water (2×50 mL). Concentration under vacuum left a solid residue which was crystallized from chloroform/ethanol (¼, 300 mL, reflux to 0° C.). Unsatisfactory analysis prompted a second recrystallization from the same solvent (160 mL) to give 1.52 g (58%) of the titled compound as pale yellow prisms (m.p. 232°–234°). $^1$H NMR (CDCl$_2$, δ) 8.05 (m, 2H, 2-phenyl-H (ortho)), 7.45 (m, 13H, phenyl-H), 6.51 (s, 1H, pyrazole-H), 6.03 (s, 2H, 4-N$CH_2$Ph), 4.87 (s, 2H, 6-NC$N_2$Ph), 4.39 (s, 2H, lactam $CH_2$); IR (mull, cm$^{-1}$) 1684, 1619, 1591, 1576; UV (ethanol) λmax(ε) 206 (42,200), 227 (23,640), 268 (32,660), 285sh (15,600), 310sh (7,900), 337 (6,030); MS m/e (rel. intens.) 447 (M+1, 8) 446 (M+, 25), 355 (7), 252 (5), 91 (100); Exact mass calc'd for $C_{28}H_{22}N_4O_2$=446.1743; Found=446.1742; Calc'd analysis=C, 75.32; H, 4.97; N, 12.55; Found=C, 74.34; H, 5.03; N, 12.32; TLC (silica, 1/1 chloroform/ethyl acetate) Rf 0.70.

EXAMPLE 9

6-Cyclohexyl-2-phenyl-4-(phenylmethyl)-5,6,7,8-tetrahydro-4H-pyrazolo[1,5-a]pyrido[3,4d]pyrimidine-5,9-dione A. 1-Cyclohexyl-2,3-dioxopiperidine-4-carboxylic acid, ethyl ester To a suspension of potassium carbonate (9.65 g, 69.9 mmole) in cyclohexylamine (8.0 mL, 69.9 mmole) was added ethyl 4-bromobutyrate (10.0 mL, 69.9 mmole) and the mixture was stirred at room temperature for 24 hours. The resulting solid mass was dissolved in methylene chloride (100 mL) and washed with water (100 mL). Evaporation of the organic phase under vacuum left a turbid oil which was dissolved again in methylene chloride (100 mL) and to it added 1 N aq. NaOH (100 mL). While cooling the mixture in a cold water bath, ethyl oxalyl chloride (7.8 mL, 70 mmole) was added and the reaction was stirred for 15 minutes. The methylene chloride layer was separated, dried over MgSO$_4$, and evaporated under vacuum, leaving an amber oil. This was dissolved ini absolute ethanol (50 mL) and to it added a solution of ethanolic sodium ethoxide (21 wt.%, 26 mL, 70 mmole). The solution was refluxed on a steam bath for 1.5 hours, cooled and then most of the solvent removed under vacuum. The resulting tan chunky solid was suspended in water (250 mL) which had been made acidic with concentrated HCl (5 mL) and stirred vigorously at room temperature overnight, turning into a flocculent, lighter colored solid. This was collected by suction filtration, washed with water, and air dried. Crystallization from 1/1 ethanol/water (100 mL) gave, after cooling to 0° C., gave the subtitled ester, 1.80 g (15%) of light tan needles (m.p. 88°–89°). A second crop from 50 mL of the same solvent gave an additional 0.55 g of the ester for a total yield of 3.35 g (18%). $^1$H NMR (CDCl$^3$, δ) 4.3 (m, 1H, NC-H), 4.25 (q, 2H, J= 7 Hz, O$CH_2$), 3.30 (t, 2H, J=7 Hz, N$CH_2$), 2.46 (t, 2H, J=7 Hz, N$CH_2CH_2$), 1.30 (t, 3H, J=7 Hz, $CH_3$), 1.1–1.9 (m, 10H); IR (mull) 1658, 1613, 1242, 1226 cm$^{-1}$; UV (ethanol) λmax (68 ) 251 (8180), 290(6730); MS m/e (rel. intens.) 267 (m+, 34), 221 (25), 193 (31), 186 (25), 150 (17), 140 (100); Exact mass calc'd for $C_{14}H_{21}NO_4$=267.1470; Found=267.1461; TLC (silica, 10% methanol/chloroform) Rf 0.7.

B.
6-Cyclohexyl-2-phenyl-4,6,7,8-tetrahydro-5H-pyrazolo[1,5-a]-pyrido[3,4-d]pyrimidine-5,9-dione The ester from part A hereinabove (2.77 g, 10.4 mmole) and 3-amino-5-phenylpyrazole, prepared as described in Preparation 1 part B hereinabove (1.75g) were combined in glacial acetic acid (11 mL) and refluxed for four hours. The reaction was cooled and diluted with 95% ethanol (50 mL). After stirring for 15 minutes, the mixture was suction filtered and the collected solid was washed twice with more ethanol. After drying under vacuum, 3.60 g (96%) of the subtitled compound was white microcrystalline solid were obtained (m.p. >320°) which was pure as judged by elemental analysis. $^1$H NMR (CDCl$_3$, δ) 8.05 (dd, 2H, J=2, 5.5 Hz, 2-phenyl H), 7.47 (m, 3H, 3,4-phenyl H), 6.52 (s, 1H, pyrazole-H), 3.61 (t, 2H, J=7 Hz, N$CH_2$), 3.01 (t, 2H, J=7 Hz, 8-$CH_2$), 12–2.0 (m, 10H); IR (mull) 3247, 3215, 1687, 1645, 1622, 1606 cm$^{-1}$; UV (ethanol) λmax(ε) 205 (27,700), 232 (24,220), 273 (34,700), 285sh (23,640), 303sh (7860), 352 (4420); MS m/e (rel. intens.) 363 (M+1, 25), 362 (M+, 100), 281 (20), 280 (75), 279 (49), 223 (12), 195 (8); Analysis calc'd for $C_{21}H_{22}N_4O_2$=C, 69.59; H, 6.12; N, 15.46; Found=C, 69.21; H, 6.26; N, 15.39; TLC (silica, 10% methanol/chloroform) Rf 0.69.

C.
6-Cyclohexyl-2-phenyl-4-(phenylmethyl)-5,6,7,8-tetrahydro-4H-pyrazolo[1,5-a]pyrido[3,4-d]pyrimidine-5,9-dione A suspension of the -4-(unsubstituted)pyrimidinedione derivative from part B hereinabove (1.47 g, 4.06 mmole), benzyl bromide (0.96 mL, 8.1 mmole), and anhydrous potassium carbonate (570 mg, 4.1 mmole) in dry DMF (21 mL) was stirred in a stoppered flask at room temperature for 24 hours. The reaction was diluted with water (100 mL), stirred for 10 minutes and suction filtered. The collected solid was washed with water and air dried. Crystallization from ethanol/chloroform (15/1, 150 mL, reflux to 0°) afforded 1.40 g (76%) of the titled product as ivory colored needles (m.p. 247°-248°). $^1$H NMR (CDCl$_3$, δ) 7.97 (m, 2H, 2-phenyl-H (ortho)), 7.2–7.5 (m, 8H, phenyl-H), 6.30 (s, 1H, pyrazole-H), 5.74 (bs, CH$_2$Ph), 4.5 (m, 1H, cyclohexyl CH), 3.45 (t, 2H, J=6 Hz, lactam NCH$_2$), 2.95 (t, 2H, J=6 Hz, NCH$_2$CH$_2$), 1.1–2.0 (m, 10H, cyclohexyl-CH$_2$); IR (mull, cm$^{-1}$) 1685, 1650, 1588, 1571; UV (ethanol) λmax(ε) 205 (38,000), 229 (23,410), 271 (33,680), 285sh (18,330), 300(9,300), 350(5,730); MS m/e (rel. intens.) 453 (M+1, 28), 452 (M+1, 61), 361 (42), 279 (14), 91(100); Found=C, 74.00; H, 6.42; N, 12.10; TLC (silica, 2/1 chloroform/ethyl acetate) Rf 0.71.

EXAMPLE 10

6-Cyclohexyl-6,7-dihydro-3-phenyl-4-(phenylmetehyl)-4H-pyrazolo[1,5-a]-pyrrolo[3,4-d]pyrimidine-5,8-dione

A.

6-Cyclohexyl-4,7-dihydro-3-phenyl-5H-pyrazolo[1,5-a]pyrrolo[3,4-d]pyrimidine-5,8(6H)-dione 4-Phenylpyrazol-3-amine [Anderson, E. L. et al., "Synthesis . . . 3-Amino-4-Arylpyrazoles", *J. Med. Chem.*, 7, (1964), pp. 259-268] (3.00 g, 18.8 mmole) and ethyl 1-cyclohexyl-4,5-dioxo-3-pyrrolidinecarboxylate (4.77 g, 18.8 mmole) were combined in glacial acetic acid (19 mL) and stirred under reflux for five hours. No precipitate was observed throughout the course of the reaction. Upon cooling, the reaction solidified to a light yellow mass which was dissolved in 95% ethanol (100 mL) at reflux and water (50 mL) was added slowly while maintaining reflux. After cooling to room temperature, the thick yellow solid was collected by suction filtration and washed with more ethanol/water. Drying under vacuum left 5.37 g homogenous by TLC. Unsatisfactory analysis prompted recrystallization from 95% ethanol (200 mL) to give 3.31 g (m.p.>148°, dec.). Yield: 51% of the subtitled compound. $^1$H NMR CDCl$_3$, δ) 8.08 (s, 1H, pyrazole-H), 7.44 (d, 2H, J=8 Hz, 2-phenyl H), 7.36 (t, 2H, J=8 Hz, 3-phenyl H), 7.23 (t, 1H, J=8 Hz, 4-phenyl H), 4.37 (s, 2H, lactam CH$_2$), 3.99 (m, 1H, cyclohexyl CH), 1.1–1.9 (m, 10H, chclohexyl CH$_2$); IR (mull) 3519, 1692, 1638, 1613, 1455 cm$^{-1}$; UV (ethanol) λmax(ε) 205 (29,400), 210sh (27,750), 237 (18,350), 268 (18,760), 370 (7700); MS m/e (rel. intens.) 349 (M+1, 23), 348 (M+, 97), 267 (18), 266 (100), 210 (8), 183 (9); Exact mass calc'd for C$_{20}$H$_{20}$N$_4$O$_2$=348.1586; Found=348.1593; TLC (silica, 10% methanol/chloroform) Rf 0.52.

B.

6-Cyclohexyl-6,7-dihydro-3-phenyl-4-(phenylmethyl)-4H-pyrazolo-[1,5-a]pyrrolo[3,4-d]-pyrimidine-5,8-dione.

A mixture of the 6-cyclohexyl-5,8-dione compound from part A hereinabove (1.83 g, 5.25 mmole) potassium carbonate (735 mg, 5.3 mmole) and benzyl bromide (1.25 mL, 10.5 mmole) in dry DMF (26 mL) was stirred in a capped flask at room temperature for 25 hours. The reaction was diluted with water (120 mL), stirred for five minutes and suction filtered. The collected solid was washed with water and air dried. The crude solid was suspended in boiling ethanol (150 mL) and chloroform added until all dissolved (approximately 70 mL). Cooling to 0° C. afforded 0.62 g of the titled compound as fine yellow needles (m.p. 293°-295°, dec.). A second crop from 3/1 ethanol/chloroform (100 mL) afforded another 0.62 g (m.p. 291°-293°, dec.). Total yield=1.24 g (56%). $^1$H NMR (CDCl$_3$, δ) 8.05 (s, 1H, pyrazole-H), 8.05 (m, 2H, 3-phenyl-H (ortho)), 7.2–7.45 (m, 7H, phenyl-H), 6.03 (s, 2H, NCH$_2$Ph), 4.29 (s, 2H, lactam CH$_2$), 4.25 (m, 1H, cyclohexyl CH), 1.1–2.0 (m, 10H, cyclohexyl CH$_2$); IR (mull, cm$^{-1}$) 1700, 1692, 1586, 1578, 1523; UV (ethanol) λmax(ε) 205 (36,000), 256 (21,730), 306 (12,240), 346 (9620); Ms m/e (rel. intens.) 439 (M+1, 18), 438 (M+60), 361 (12), 347 (16), 265 (11), 91 (100); Analysis calc'd for C$_{27}$H$_{26}$N$_4$O$_2$=C, 73.95; H, 5.98; N, 12.78; Found=C, 73.50; H, 618; N, 12.89; TLC (silica, 2/1 chloroform/ethyl acetate) Rf 0.50.

EXAMPLE 11

4-(Benzoylmethyl)-2-(4-chlorophenyl)-6-cyclohexyl-6,7-dihydro-4H-pyrazolo[1,5-a]pyrrolo[3,4-d]pyrimidine-5,8-dione

A.

2-(4-Chlorophenyl)-6-cyclohexyl-4,7-dihydro-5H-pyrazolo[1,5-a]pyrrolo[3,4-d]pyrimidine-5,8-(6H)-dione 4-(p-Chlorophenyl)-3-amino-pyrazole (3.29 g, 17.0 mmole) and ethyl 1-cyclohexyl-4,5-dioxo-3-pyrrolidinecarboxylate (4.31 g, 17.0 mmole) were combined in glacial acetic acid (17 mL) and refluxed for four hours. After cooling, the reaction was diluted with 95% ethanol (120 mL), stirred for 15 minutes and suction filtered. The cream-colored powdery solid collected was washed twice with more ethanol and then dried under vacuum, leaving 5.37 g (83%) of the subtitled compound, pure as judged by elemental analysis (m.p.>320°). $^1$H NMR-compound was too insoluble for a satisfactory spectrum; IR (mull) 1693, 1673, 1640, 1612, 1441 cm$^{-1}$; UV (ethanol) λmax(ε) 208 (26300), 230 (24800), 265sh (34850), 274 (40300), 283 (32350), 305 (9160), 320 (6880), 345 (6230); MS m/e (rel. intens.) 384 (M+2, 37), 383 (M+1, 24), 382 (M+, 100), 339 (17), 300 (78), 244 (13); Analysis calc'd for C$_{20}$H$_{19}$N$_4$O$_2$Cl=C, 62.75; H, 5.00; N, 14; Cl, 9.26; Found=C, 62.84; H, 5.15; N, 14.66; Cl, 9.41.

B.

4-(Benzoylmethyl)-2-(4-chlorophenyl)-6-cyclohexyl-6,7-dihydro-4H-pyrazolo[1,5-a]pyrrolo[3,4-d]pyrimidine-5,8-dione The pyrazole derivative compound from Part A hereinabove (3.0 g, 7.84 mmole), 2-chloroacetophenone (2.42 g, 15.68 mmole) and potassium carbonate (1.13 g, 8.20 mmole) were stirred in DMF (41 ml) for 20 hours at room temperature. Water was added to the reaction mixture (205 ml ) and the resulting lumpy solid was collected by filtration, washed with water (3×) and air dried. The solid was recrystallized from 95% ethanol (200 ml) and chloroform (150 ml). The resulting white crystals were filtered and vacuum dried to afford 1.58 g (40%) of the titled compound (m.p. 237°-239°). $^1$H NMR (CDCl$_3$, δ) 8.1 (d, 2H, CO(-o-phenyl-H)), 7.9 (d, 2H, pyrazole(o-phenyl-H)) 7.7–7.8 (m, 1H, CO(-p-phenyl-H)), 7.5 (m, 2H, CO(m-phenyl)), 7.3–7.4 (m, 2H, pyrazole(m-phenyl)), 6.30 (s, 1H, pyrazole-H)), 6.14 (s, 2H, CH$_2$CO), 4.42 (s, 2H, lactam CH$_2$), 4.0–4.2 (m, 1H, cyclohexyl-H), 1.3–2.0 (m, 10H, cyclohexyl CH$_2$); IR (mull) 1725, 1700, 1675, 1625, 1580, 1565, 1438 cm$^{-1}$; UV (ethanol) λmax(ε) 250 (37700), 271 (36860), 290 sh (29560), 297 sh (15700), 335 (7960); MS m/e (relative intensity) 501 (M+, 15), 105 (100), 500 (45), 502 (17), 106 (17), 77 (17), 83 (16), 395 (15); Analysis calc'd for C$_{28}$H$_{25}$N$_4$O$_3$Cl=C, 67.13; H, 5.03; N, 11.18; Cl, 7.08; Found C, 67.06; H, 5.04; N, 11.23; Cl, 7.50.

EXAMPLE 12

4-(Ethoxycarbonylpropyl)-6-cyclohexy-4,7-dihydro-2-phenyl-5H-pyrazolo[1,5-a]pyrrolo[3,4-d]pyrimidine-5,8(6H)-dione A mixture of 100 g (2.87) mmole) of 6-cyclohexyl-4,7-dihydro-2-phenyl-5H-pyrazolo[1,5-a]pyrrolo[3,4-d]pyrimidine-5,8-dione (see preparation 1), 0.82 ml. (5.7 mmoles), of ethyl 4-bromobutyrate and 0.41 g., 3.0 mmole of potassium carbonate in 11 ml. of -dimethyl-sulfoxide (DMSO) was stirred at 50° C. for 16.5 hours. Then 35 ml. of water was added and the mixture was suction filtered. The collected solid was washed with more water and air dried. The crude solid was recrystallized from 95% ethanol (100 ml), reflux cooled to room temperature, affording 1.11 g (84% yield) of the titled compound as very fine white needles, m.p. 195°–196° C. 1H NMR (CDCl$_3$, δ) 8.06 (d, 2H, phenyl-H (ortho), 7.45 (m, 3H, phenyl-H), 6.70 (s, 1H, pyrazole-H, 4.74 (t, 2H, J=Hz, 4-NCH$_2$), 4.37 (s, 2H, lactam CH$_2$), 4.16 (q, 2H, J=7 Hz, OCH$_2$), 4.15 (m, 1H, 6-NCH), 2.49 (t, 2H, CH$_2$CO$_2$C$_2$H$_5$), 2.23 (m, 2H, CH$_2$), 1.15–1.95 (m, 10H, cyclohexyl CH$_2$), 1.26 (t, 3H, J"7 Hz, CH$_3$.

EXAMPLE 13

6-Cyclohexyl-6,7-dihydro-4-[2-(hydroxyimino)-2-phenyl-ethyl]-2-phenyl-4H-pyrazolo[1,5-a]pyrrolo[3,4-d]pyrimidine-5,8-dione A mixture of 4-(benzoylmethyl)-6-cyclohexyl-6,7-dihydro-2-phenyl-4H-pyrazolo[1,5-a]pyrrolo[3,4-d]pyrimidine-5,8-dione (see Example 4), (1.00 g.; 2.15 mmoles) and hydroxylamine hydrochloride (225 mg.; 3.23 mmole), in 4.5 ml of absolute ethanol and 1.5 of pyridine was heated to reflux, becoming homogenous. The solution deposited a precipitate with time, so another 2 ml. of ethanol was added to aid stirring. After a total of eight hours at reflux, the mixture was cooled and diluted with 15 ml. of ethanol. The mixture was suction filtered through a medium glass frit and the collected solid was washed with ethanol and dried in vacuo. The crude solid was suspended in boiling 95% ethanol (400 ml.), and chloroform was added until dissolution was achieved (70 ml.). About 50 ml. of the resulting solvent mixture was then boiled off before cooling to room temperature. This procedure afforded 624 mg. (60% yield) of the titled compound, m.p. >280° C. The NMR spectral analysis of a sample of this material indicated that a 1:1 mixture of the titled oxime isomers had been obtained. 1H NMR (DMSO d6, δ) (mixture of oxime isomers) 12.14 (s, 1H, OH), 11.12 (s, 1H, OH), 8.01 [d, 2H, J=7 Hz, 2-phenyl-H (ortho)], 7.89 (d, 2H, J=7 Hz, oxime-phenyl-H (ortho)], 7.2–7.7 (m, 17H, phenyl-H and pyrazole-H of one isomer), 6.76 (s, 1H, pyrazole-H), 6.12 (bs, 2H, (C(NOH)CH$_2$), 5.72 (bs, 2H, C(NOH)CH$_2$), 4.41 (s, 2H, NCH$_2$), 4.30 (s, 2H, NCH$_2$), 4.0 (m, 2H, cyclohexyl CH of both isomers), 1.1–1.9 (m, 20H, cyclohexyl CH$_2$ of both isomers).

EXAMPLE 14

6-Cyclohexyl-6,7-dihydro-4-(2-hydroxy-2-phenylethyl)-2-phenyl-4H-oyrazolo[1,5-a]pyrrolo[3,4-d]pyrimidine-5,8-dione A mixture of 0.50 g (1.44 mmole) of 6-cyclohexyl-4,7-dihydro-2-phenyl-5H-pyrazolo[1,5-a]pyrrolo[3,4-d]pyrimidine-5,8-(6H-dione (see Preparation 1), 0.30 ml. (2.2 mmoles) of triethylamine and 0.33 ml. (2.9 mmole) of styrene oxide in 6 ml. of absolute ethanol was stirred at reflux for 16 hours, turning dark brown over that time. The reaction mixture was cooled and diluted with 90 ml. of 95% ethanol. After stirring for five minutes, the mixture was suction filtered through a medium glass frit and the collected solid was washed with more ethanol and air dried. The crude solid was suspended in 50 ml. of boiling ethanol and chloroform was added until dissolution was achieved (required 20 ml.). The mixture was cooled to 0° C. which caused a precipitation to give 205 mg. (30% yield) of the titled compound as a light tan solid, m.p. 263°–266° C. 1H NMR (CDCl$_3$, δ) 7.98 (d, 2H, J=8 Hz, 2-phenyl-H (ortho), 7.56 (d, 2H, J=7 Hz, phenyl-H), 7.3–7.5 (m, 6H, phenyl-H), 6.41 (s, 1H, pyrazole-H), 5.27 (m, 1H, CHOH), 4.98 (dd, 1H, J=9.13 Hz, NCH$_2$), 4.62 (dd, 1H, J=3, 13 Hz, NCH$_2$), 4.34 (s, 2H, lactam NCH$_2$), 4.14 (m, 1H, cyclohexyl OH), 3.81 (d, 1H, J=6 Hz, OH), 1.1–2.0 (m, 10H, cyclohexyl CH$_2$).

EXAMPLE 15

6-Cyclohexyl-6,7-dihydro-2-[4-(2-propenyloxy)-phenyl]-4-phenylmethyl-4H-pyrazolo[1,5-a]pyrrolo[3,4-d]pyrimidine-5,8-dione

A. 2-Cyano-1-[4-(2-propenyloxy)phenyl]ethanone

A mixture of 41.25 g. (200 mmoles) of ethyl 4-[(2-propenyl)oxy]phenylbenzoate, 15.0 g. (220 mmoles) of sodium ethoxide and 13 ml. (240 mmoles) of acetonitrile in 85 ml. of dry toluene was mechanically stirred under a nitrogen atmosphere at 108° C. for 24 hours. The reaction mixture was cooled and diluted with 600 ml. of water. After all of the solid had dissolved, the mixture was washed with two 100 ml. portions of ethyl ether. The aqueous phase was then acidified to pH 5–6 with concentrated aqueous hydrochloric acid (required about 15 ml.). The precipitate which formed was collected by suction filtration, washed with water and air dried. This solid was sufficiently pure to carry directly into the next step. If desired, an analytically pure sample could be obtained by crystallization from an ethyl acetate/hexane mixture. 1H NMR (CDCl$_3$, δ) 7.90 [d, 2H, J=9 Hz, phenyl-H(2]), 6.99 (d, 2H, J=9 Hz, phenyl-H(3)), 6.05 (m, 1H, vinyl CH), 5.43 (d, 1H, J=17 Hz, vinyl CH$_2$), 5.35 (d, 1H, J=11 Hz, vinyl CH$_2$), 4.63 (d, 2H, J=5 Hz, OCH$_2$), 4,02 (s, 2H, CH$_2$CN).

B. 5-[4-(2-Propenyloxy)phenyl]pyrazol-3-amine

To a solution of 22.5 g. (approximately 85% pure, 110 mmoles) of part A hereinabove in 150 ml. of 95% ethanol, there was added 6.8 ml (140 mmoles) of hydrazine monohydrate. The resulting mixture was then stirred at reflux for two hours. The reaction mixture was cooled to 0° C., depositing a crystalline precipitate. The precipitate was collected by suction filtration, washed with cold ethanol and dried in vacuo, affording 15.07 g. (74% yield) of the pure subtitled compound, m.p. 158°–159° C. 1H NMR (DMSO, d6, δ) 7.55 (d, 2H, J=9 Hz, phenyl-H(2)), 6.95 (d, 2H, J=9 Hz, phenyl-H(3)), 6.04 (m, 1H, vinyl(H), 5.68 (bs, 1H, pyrazole-H), 5.04 (dd, 1H, J=16, 2 Hz, vinyl CH$_2$), 5.26 (dd, 1H, J=11, 2 Hz, vinyl CH$_2$), 4.57 (d, 2H, J=5 Hz, OCH$_2$).

C.

6-Cyclohexyl-6,7-dihydro-2-[4-(2-propenyloxy)-phenyl]-4H-pyrazolo[1,5-a]pyrrolo[3,4-d]pyrimidine-5,8-dione A mixture of the pyrazole amine derivative from part B hereinabove (14.07 g; 65.4 mmoles) and ethyl 1- cyclohexyl-4,5-dioxo-3-pyrrolidinecarboxylate ester (19.21 g; 71.9 mmole) in 95% ethanol (70 ml.) was stirred at reflux for 24 hours. The mixture was diluted with more ethanol (150 ml.) and then suction filtered. The collected solid was washed with more ethanol and dried in vacuo, leaving 23.65 g. of the subtitled compound as a white microcrystalline solid, 89% yield, m.p. >320° C. 1H NMR (DMSO d6, δ) 7.91 (d, 2H, J=8 Hz, phenyl-H), 7.04 (d, 2H, J=8 Hz, phenyl-H), 6.58 (s, 1H, pyrazole-H), 6.07 (m, 1H, vinyl CH), 5.42 (d, 1H, J=18 Hz, vinyl CH₂), 5.28 (d, 1H, J=10 Hz, vinyl CH₂), 4.63 (d, 2H, J=4 Hz, OCH₂), 3.96 (m, 1H, NCH), 1.1–1.9 (m, 10H, CH₂)

D.
6-Cyclohexyl-6,7-dihydro-2-[4-(2-propenyloxyphenyl)-4-phenyl-methyl-4H-pyrazolo[1,5-a]pyrrolo[3,4-d]pyrimidine-5,8-dione A mixture of 10.0 g (24.7 mmoles) of 6-cyclohexyl-6,7-dihydro-2-[4-(2-propenyloxy)phenyl]-4H-pyrazolo[1,5-a]pyrrolo[3,4-d]pyrimidine-5,8-dione (from part C hereinabove) 5.9 ml (49.5 mmoles) of benzyl bromide and 3.76 g (27 mmoles) in 100 ml. of N,N-dimethylformamide (DMF) was stirred at room temperature for 24 hours. The turbid yellow mixture which resulted was poured into 300 ml. of vigorously stirred water. The mixture was stirred for five minutes and then suction filtered and the collected solid was air dried. The crude solid was suspended with 1000 ml. of boiling ethanol and chloroform was added until dissolution was achieved (approximately 150 ml.). Cooling the mixture to 0° C. gave 11.37 g (93% yield) of the titled compound as pale yellow fine needle crystals, m.p. 226°–227° C. 1H NMR (CDCl₃), δ) 7.89 (d, 2H, J=9 H₂, 2-phenyl-H), 7.33 (m, 5H, phenyl-H), 6.95 (d, 2H, J=9 Hz, 2-phenyl-H), 6.35 (s, 1H, pyrazole-H), 6.05 (m, 1H, vinyl (H), 5.90 (s, 2H, CH₂phenyl), 5.43 (d, 1H, J=17 Hz, vinyl CH₂), 5.30 (d, 1H, J=10 Hz, vinyl CH₂), 4.57 (d, 2H, J=5 Hz, OCH₂), 4.38 (s, 2H, lactam CH₂), 4.16 (m, 1H, NCH), 1.1–2.0 (m, 10H, CH₂).

EXAMPLE 16

6-Cyclohexyl-6,7-dihydro-2-(4-hydroxyphenyl)-4-phenyl-methyl-4H-pyrazolo[1,5-a]pyrrolo[3,4-d]pyrimidine-5,8-dione To a suspension of 10% palladium on carbon (0.40 g) catalyst in 95% ethanol (50 ml) there was added 2.00 g (4.05 mmoles) of 6-cyclohexyl-6,7-dihydro-2-[4-(2-propenyloxy)phenyl]-4-phenylmethyl-4H-pyrazolo[1,5-a]pyrrolo[3,4-d]pyrimidine-5,8-dione (see Example 14 hereinabove) and then 0.18 ml. (2.0 mmoles) of 70% aqueous perchloric acid. The resulting mixture was stirred at reflux for 21 hours. Thin layer chromatography (TLC) analysis of a sample of the reaction mixture indicated that the reaction was incomplete so another 0.2 ml of perchloric acid was added and refluxing was continued for another eight hours. The reaction mixture was cooled and diluted with 70 ml. of chloroform, dissolving all the solid except the catalyst. The resulting mixture was filtered through a filter aid (Celite ®) and then concentrated by boiling to a volume of about 75 ml. Cooling the residue to 0° C. for several days provided 1.25 g. (68% yield) of the titled compound as off-white prism crystals, m.p. 307°–310° C. dec.). 1H NMR (DMSO d6, δ) 7.77 (d, 2H, J=8 Hz, 2-phenyl-H), 7.35 (m, 5H, phenyl-H), 6.85 (d, 2H, J=8 Hz, 2-phenyl-H), 6.83 (s, 1H, pyrazole-HO, 5.87 (s, 2H, CH₂ phenyl), 4.38 (s, 2H, lactam CH₂), 3.96 (m, 1H, NCH), 1.1–1.9 (m 10H, CH₂).

EXAMPLE 17

6-Cyclohexyl-6,7-dihydro-4-[2-(hydroxyimino)-2-phenylethyl]-2-phenyl-4H-pyrazolo[1,5-a]pyrrolo3,4-d]pyrimidine-5,8-dione (11.3 g, 23.0 mmole), heptanoic anhydride (11.5 mL, 47.2 mmole) and 4-dimethylaminopyridine (2.9 g, 23.4 mmole) were stirred at room temperature in methylene chloride (260 mL) for 4½ hours. The reaction mixture was diluted with methylene chloride (100 mL) and washed successively with 1.0M aq. HCl (300 mL), water (300 mL), sat. aq. sodium bicarbonate (300 mL), and water (300 mL). The organic phase was dried over magnesium sulfate and concentrated in vacuo, leaving 19.9 g of a white solid consisting of a mixture of geometric isomers about the oxime ester. The isomers could be separated by flash chromatography (10% ethyl acetate/hexane) to provide pure samples of 6-cyclohexyl-6,7-dihydro-4-[2-{[(1-oxoheptyl)oxy]imino}-2-phenylethyl]-2-phenyl-4H-pyrazolo[1,5-a]pyrrolo[3,4-d]pyrimidine-5,8-dione (less polar isomer, m.p. 224°–225°) and 6-cyclohexyl-6,7-dihydro- 4-[2-{[(1-oxoheptyl)oxy]imino}-2-phenylethyl]-2-phenyl-4H-pyrazolo[1,5-a]pyrrolo[3,4d]pyrimidine-5,8-dione (more polar isomer, m.p. 151°–154°). Alternatively, the crude mixture of isomers could be recrystallized directly from ethanol/chloroform to provide 7.84 g (56) of the mixture as white crystals (m.p. 206°–209°). 6-cyclohexyl-6,7-dihydro-4-[2-{[(1-oxoheptyl)oxy]imino}-2-phenylethyl]-2-phenyl-4H-pyrazolo[1,5-a]pyrrolo[3,4-d]pyrimidine-5,8-dione, 1H NMR (CDCl₃) 7.9–8.0 (m, 2H), 7.3–7.5 (m, 8H), 6.43 (s, 1H), 6.33 (bs, 2H), 4.27 (s, 2H), 4.1–4.3 (bs, 1H), 2.61 (t, 2H), 1.1–2.0 (m, 18H), 0.8–1.0 (m, 3H). 6-cyclohexyl-6,7-dihydro-4-[2-{[(1-oxoheptyl)-oxy]imino}-2phenylethyl]-2-phenyl-4H-pyrazolo[1,5-a]pyrrolo[3,4-d]pyrimidine-5,8-dione (more polar isomer, m.p. 151°–154°) 8.1–8.2 (m, 2H), 7.2–7.7 (m, 8H), 6.91 (s, 1H), 6.14 (bs, 2H), 4.23 (s, 2H), 4.1–4.2 (bs, 1H), 2.30 (t, 2H), 1.1–2.0 (m, 18H), 0.8–1.0 (m, 3H).

Utilizing a procedure similar to that of Example 17, but substituting the appropriate anhydride for heptanoic anhydride, there is obtained 6-cyclohexyl-6,7-dihydro-4-[2-{[(1-oxoocyl)oxy]imino]-2-phenylethyl}-4H-pyrazolo[1,5-a]pyrrole[3,4-d]pyrimidine-5-8-dione, a 1.4:1 mixture of geometric isomers about the oxime ester, a 1:1 mixture of isomers 6-cyclohexyl-6,7-dihydro-4-[2-{[(1-oxododecyl)-oxy]imino}-2-phenylethyl]-2-phenyl-4H-pyrazolo[1,5-a]pyrrolo[3,4-d]pyrimidine-5-8-dione and 6-cyclohexyl-6,7-dihydro-4-[2-{[(1-oxododecyl)oxy]imino}2-phenylethyl]-2-phenyl-4H-pyrazolo[1,5- a]pyrrolo[3,4-d]pyrimidine-5,8-dione (less polar isomer).

The compounds of this invention described and exemplified herein for use in the pharmaceutical composition forms and in the method of treatment aspects of this invention are expected to be useful as the active drug ingredient in drug formulations used to treat a valuable warm-blooded animal patient, including humans, horses, dogs, cats, goats, pigs and the like, for the reduction or prevention and control of cholesterol buildup, for treating atherosclerosis conditions, for lowering blood serum cholesterol, for altering the relative distribution of circulating free and esterified high density (HDL) and low density lipo-protein-bound cholesterol (LDL) fractions, and for the reduction of cholesterol deposition in arterial tissues.

The selected drug compound used according to the method of this invention can be administered orally or systemically, neat, but most usually in combination with one or more pharmaceutical composition ingredients in the form of tablets, hard and soft filled gelatin capsules, caplets and/or in sterile solutions administered by sterile intramuscular or intravenous procedures. The effective dosage of one or more of these selected compounds is expected to be in the range from about one to about 20 mg. of the active drug compound (I) per kilogram of body weight of the patient per day, depending upon the drug compound (I) selected, the patient body weight, the severity of the condition being treated and other factors of concern to the patient's physician until the atheroscllerotic condition or the HDL/LDL ratio improves. It is expected that the selected compound of this invention would most probably by formulated into compositions for oral tablet, capsule or suppository administration forms in sizes to contain from 0.5 to 1000 mg of the compound (I) per tablet or capsule for use a the animal patient and condition requires.

A standard in vitro test system designed to identify compounds capable of inhibitory the ACAT enzyme in cultured Fu5AH rat hepatoma cells which was used to test the compounds of this invention, among others, is described hereinbelow.

In our view the esterification of arterial cholesterol in a warm-blooded animal by the ACAT enzyme represents a key reaction in the development of atherosclerosis and the inhibition of the cholesterol esterification by a selected drug represents a potential therapeutic approach to modifying the development of atherosclerosis. Furthermore, ACAT enzyme activity in intestinal tissue is important in biological process of cholesterol absorption and as such its inhibition by ACAT enzyme active drugs may reduce cholesterol absorption and thereby lower circulating levels of plasma cholesterol in man and animals.

Since the ACAT enzyme in Fu5AH cells is similar if not identical to the ACAT enzyme in arterial tissue in valuable, warm-blooded animals, including humans, the Fu5AH cell test represents a more efficient, simplified and economical means of screening for ACAT inhibitors than similar assays which depend upon the use of arterial tissue and arterial subfractions as the source of the ACAT enzyme.

For our in vitro test the Fu5AH rat hepatoma cell line was selected as our source of the ACAT enzyme since this particular cell line mimicked important characteristics of human and valuable animal arterial cells during the development of atherosclerosis. The Fu5AH cells accumulate cholesterol extensively when incubated with hyperlipemic plasma proteins; more importantly, Fu5HA cells accumulated the cholesterol predominantly as the esterified form through the action of the ACAT enzyme. See Rothblat, G. H., "Cholesteryl Ester Metabolism in Tissue Culture Cell. I. Accumulation in Fu5AH Rat Hepatoma Cells", *Lipids,* 9, (1974) page 526.

The Fu5AH cells used in our in vitro assay were first acquired from G. H. Rothblat, supra, of the Medical College of Pa.

The seed cultures were used to establish our own Fu5AH cultures and have been successfully passaged here since mid-Jul. 1984. The cells have been successfully used to evaluate over 2500 compounds since Oct. 1984 and have identified 226 ACAT inhibitors provided by chemists associated with us.

Culturing Methods and Assay Details

A. Maintenance of Stock Cultures

The Fu5AH rat hepatoma cell-line was derived from the Reuber H-35 rat hepatoma. (See Reuber, M.D., "A Transplantable Bilesecreting Hepatocellular Carcinoa in the Rat", *J. Natl., Cancer Inst.,* 26 (1961), page 891. The cell-line is maintained in Eagle's Minimal Essential Medium (MEM, GiBCO) supplemented with 5% bovine fetal calf serum. Incubation is at 36° C. in an atmosphere of 5% $CO_2$ in air (Hotpack, Model 351922). Cells from stock cultures, grown to confluency in 25 $cm^2$ flasks (Falcon) containing 10 ml. medium, are detached with 0.25% trypsin in 1% ethylenediaminetetraacetic acid (EDTA) (Gibco), diluted 1:10 with MEM and mixed by agitation through a pipette which serves to disrupt the cellular clumps. Stock cultures are replenished with fresh medium at 3 to 4 day intervals.

B. Preparation of Cultures and Culture Medium For Assay of ACAT

One ml. aliquots of the diluted stock suspension described above are then transferred to 60 mm. dishes (Falcon) containing four ml. MEM and the seeded cells are allowed to grow to confluence (three days). At confluence, the medium is removed by aspiration and the cells are washed once with MEM. Five ml. of MEM supplemented with 5% hyperlipemic rabbit serum (HRS) (HRS is obtained from male New Zealane rabbits fed Purina Chow ® rabbit feed supplemented with 1% cholesterol and 3% peanut oil (w/w/w/) for two to three weeks. Pooled sera from two or more rabbits are filtered through a 0.45 m$\mu$ filter (Nalgene) and stored frozen in convenient aliquots until used) and containing 1$\mu$ Ci/ml of $^3$H-cholesterol are then added to the dishes as the experimental (assay) medium. The experimental medium is labeled with 1,2-$^3$H(N)-cholesterol (sp. act. approx. 40-60 Ci/mol, New Zealand Nuclear Corp.) prior to its addition to the confluent cultures and is prepared as follows. Five ml. of HRS is diluted with approximately 20 ml of MEM and the mixture is labeled by the addition of 100 $\mu$Ci $^3$H-cholesterol dissolved in 100 $\mu$l absolute ethyl alcohol. The resulting mixture is then incubated for four hours at 36° C. to permit equilibration of the labeled cholesterol with the serum lipoprotein-cholesterol. After the equilibration period, the mixture is diluted to 100 ml. with MEM and used as the labeled assay medium. Following the addition of the labeled medium to the dishes, dimethylsulfoxide solutions of the test substances and the positive standard chloropromazine HCl (1 mg/ml) are added to the cultures in volumes of 25, 50, 75 $\mu$l to yield final drug concentrations of 5, 10 and 15 $\mu$g/ml; control cultures receive equivalent volumes of dimethylsufoxide alone. The assay cultures are incubated 18 hours under a 5% $CO_2$ atmosphere as above after which time the media are removed by aspiration and the cells washed three times with 3 ml of phosphate-buffered saline (Dulbecco's, Gibco).

Analysis of Cultures

Following the last wash, 2 ml of isopropanol (propanol-2, Burdick and Jackson) are added to the culture dishes and the cellular cholesterol and cholesteryl esters are permitted to extract for 15 minutes at room temperature. Following extraction, a 50 $\mu$l aliquot of each extract is chromatographed by thin layer chromatography on silica gel G coated glass plates (Brinkman) in order to fractionate cholesterol and cholesteryl esters (10). Cholesterol and cholesteryl esters are visualized by spraying the plates with rhodamine 6G (0.05% in ethanol) and the respective regions are scraped into vials containing 15 ml Liquifluor (New England Nuclear Corp.) for radioactive assay by liquid scintillation counting (Beckman Model LS9800 Liquid Scintillation Spectrometer). In addition a 200 µl aliquot of each culture extract is dissolved in ACS II(American-Corp.) and assayed for radioactivity as above to permit calculation of total $^3$H-cholesterol uptake by the culture; this value is databased for storage along with all raw data but is not otherwise reported.

Expression of Data

The ratio of $^3$H-Cholesteryl ester radioactivity to the sum of the $^3$H-Cholesterol plus $^3$H-Cholesteryl ester recovered in the chromatographed cellular extracts×100 yields the percent of total $^3$H-cholesterol taken up which was esterified by cellular ACAT and is referred to as percent ACAT. Values less than control values identify assay cultures in which ACAT was inhibited; the positive standard values provide a basis for relative potency evaluation (in addition to monitoring the quality of a given run). Control values for percent ACAT typically range from 60%–70% under our conditions. Percent inhibition of ACAT enzyme is also easily calculated from the data using the simple formula $$1 - \frac{\% \text{ cholesterol esterified in drug treated assay}}{\% \text{ cholesterol esterified in control assay}} \times 100 = \% \text{ inhibition}$$

Criteria for Classification of a Compound as "Active"

ACAT activity in cultures treated with test compounds at three different concentrations (5, 10 and 15 µg/ml) is compared to ACAT activity in control cultures. Additionally, treatment to control ratios are compared to the performance of a positive standard (chlorpromazine) to determine activity. Compounds with ACAT inhibiting activity equal to, or greater than, that of chloropromazine are declared active, that is, of further interest for possible advanced testing, although this is an arbitrary cutoff, dictated by our practical interest, as well as constraints on economic, time and available manpower factors.

In actual fact, from a biological utility point of view, compounds inhibiting the ACAT enzyme at levels of 5% of greater can be called active in this test, but are not often tested further for other practical reasons.

Discussion

The identification of ACAT as a key enzyme in the atherogenic process and the targeting of efforts to specifically select for compounds that inhibit ACAT represent an example of a rational approach to drug discovery. In the case of this particular enzyme, considerable exploratory (basic) research was necessary to demonstrate the potential benefits of modifying ACAT activity.

Compounds discovered to be active ACAT inhibitors in the Fu5AH cell screen will be subsequently tested for anti-atherosclerotic activity in animal models of atherosclerosis.

Table I attached hereto provides test result data for detailed example compounds hereinabove in the in vitro ACAT enzyme test described first above at doses 5, 10 and 15 micrograms/ml. The data indicate that some of the compounds are more active than others, indicated by higher percentage ACAT enzyme inhibition by the exampled test compound. As indicated above, the compound of Example 4 appears to be the most potent compound for this ACAT enzyme inhibition use as a drug to control cholesterol uptake by the warm-blooded animal. Some of the data for some of the compounds appear to indicate that the test compound was not "active" at the higher dosages while the compound was "active" at the lower dosage. We believe that this phenomenon in those cases is due to lack of solubility of the drug in the test vehicle preparation or that the test cell has reached the limit of its ability to absorb the drug, or to other similar biological reasons.

In Vivo Testing

Male SEA Japanese quail, approximately four to six weeks of age, were reared at Miles Quail Farm, Gobles, Mich. from a colony of animals originally derived at The Upjohn Company. Birds were randomly distributed into ten groups of ten quail each. They were house individually in ten cage units and fed a commercial diet (Purina Game Bird Layena, Ralston Purina Co., St. Louis, Mo.) mixed with various amounts of cholesterol with and without 1% peanut oil. Compounds were mixed into 2.4 kg of the diet using a feed mixer (Hobard A-200) for twenty minutes. Control groups received normal diet. In one series of experiments birds were fed 0.5% cholesterol/1% peanut oil plus colestipol hydrochloride. After two weeks on the diets, each bird was bled from the right jugular vein and serum samples were obtained after low speed centrifugation. Food intake was determined for each group by subtracting the weight of diet remaining at the end of the experiment from the weight of the starting diet.

Beta- and alpha-lipoproteins were isolated from individual serum samples using PEG-8000 and glycerine buffer, pH 9 (9). Three hundred microliters of serum were mixed with 300 microliters of solution. A (20 grams of PEG-8000 plus 100 ml of glycerine buffer, pH 9) using a Micromedic automatic pipet. Samples were allowed to stand at room temperature for ten minutes and then were centrifuged for twenty minutes at 2000× g at 4° C. The beta-lipoprotein pellet was dissolved in 300 microliters of solution B (10 ml Triton X-100 plus 1000 ml Milli Q water). Cholesterol, triglycerides and total protein in alpha- and beta-lipoproteins were measured using the Deman Autoanalyzer, Model AU 500 (Cooper Biomedical Inc.) and Worthington Demand Enzymatic reagents.

All data were statistically analyzed using a one-way classification design. Values were transformed to logarithms to achieve more homogenous within-group variances. The mean response for each diet and for the effect was compared with the mean observed in the control animals by the LSD test. Treated/control ratios of antilogs of the log means are also presented. A P-value less than 0.004 is considered significantly different from control. See Table 2 attached hereto.

This invention also relates to compositions containing a formula I compound as an active ingredient in a pharmaceutical carrier. The compositions are useful in pharmaceutical dosage unit forms of the formula I compounds for systemic administration (oral, rectal and parenteral administration form) in therapy for treating and alleviating symptoms of atherosclerosis, elevated cholesterol levels and/or other than normal HDL/LDL lipoprotein-bound cholesterol ratios, in blood serum fractions in humans and valuable animals, including dogs, cats and other commercially valuable and domestic animals.

The term "dosage unit form" as used in this specification and in the claims refers to physically discrete units suitable as unitary dosages for mammalian subjects, each unit containing a predetermined quantity for the essential active ingredient compound of this invention calculated to produce the desired effect, in combination with the required pharmaceutical means which adapt the said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification under exemplified embodiments, these being features of the present invention. Examples of suitable dosage unit forms in accordance with this invention are tablets, intradermal implants, skin patches (transdermal applications), capsules, orally administered liquid preparations in suitable liquid vehicles, sterile preparations in suitable liquid vehicles for intramuscular and intravenous administration, suppositories and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, actose, kaolin, dicalcium phosphate, gelatin, acacia, corn syrup, corn starch, talc and the like. Capsules, both hard and soft, are filled with compositions of the selected formula I compound or salt thereof ingredients in combination with suitable diluents and excipients, for example, edible oils, talc, calcium carbonate and the like and also calcium and/or magnesium stearate. Liquid preparations for oral administration are prepared in water or aqueous vehicles which advantageously contain suspending agents, for example, methylcellulose, acacia, polyvinylpyrolidone, polyvinyl alcohol and the like. In the case of injectable forms, the injectable formulation must be sterile and must be fluid to the extent that easy syringe-ability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 mg to about 1000 mg of the essential active ingredient per dosage unit form, for administration to the patient one or more times per day, or slowly but continuously by intravenous drip methods in severe cases, depending upon the medical condition being treated, the age and weight of the patient and other factors of concern to the patient or his or her physician.

GENERAL FORMULA OF COMPOUNDS

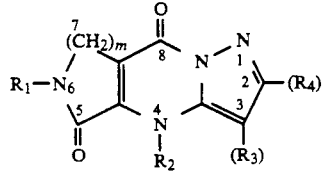

OUTLINE OF PROCESS
FOR MAKING THE COMPOUNDS

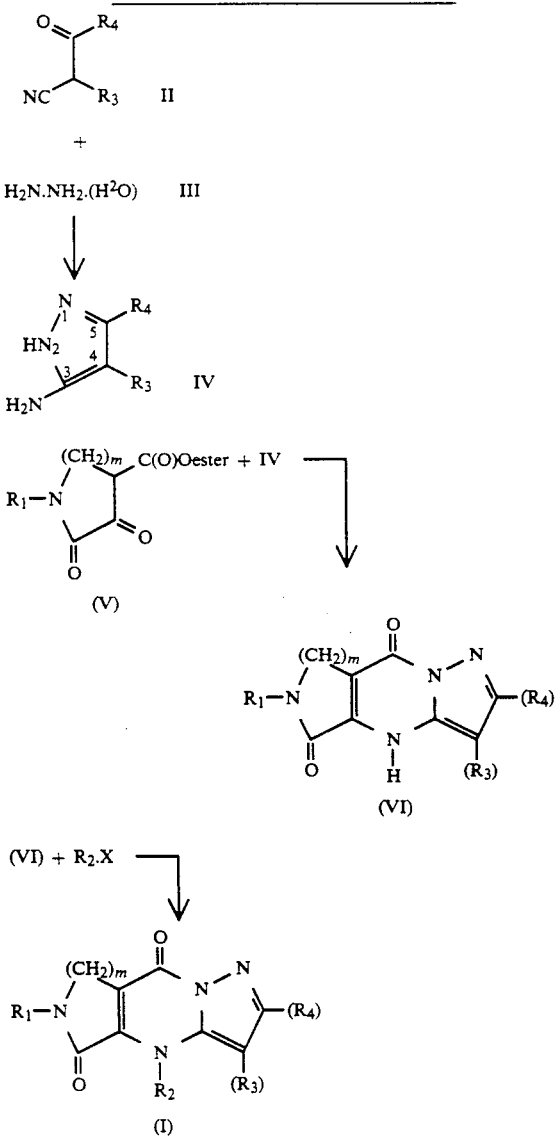

TABLE I

| Example No. | % Inhib. of Chol. Esterf. | Activity | Dose ug/ml |
|---|---|---|---|
| 2 | 60.1 | Active | 5.0 |
|   | 87.7 | Active | 10.0 |
|   | 93.6 | Active | 15.0 |
| 1 | 68.6 | Active | 5.0 |
|   | 93.2 | Active | 10.0 |
|   | 96.1 | Active | 15.0 |
| 6 | 49.8 | Active | 5.0 |
|   | 75.4 | Active | 10.0 |
|   | 87.2 | Active | 15.0 |
| 7 | 21.2 | Active | 5.0 |
|   | 17.6 | Inactive | 10.0 |
|   | 15.0 | Inactive | 15.0 |
| 3 | 43.4 | Active | 5.0 |
|   | 48.2 | Active | 10.0 |
|   | 49.2 | Active | 15.0 |
| 8 | 60.8 | Active | 5.0 |
|   | 89.5 | Active | 10.0 |
|   | 92.3 | Active | 15.0 |
| 4 | 88.6 | Active | 5.0 |
|   | 92.2 | Active | 10.0 |
|   | 91.9 | Active | 15.0 |
| 9 | 53.2 | Active | 5.0 |
|   | 82.1 | Active | 10.0 |
|   | 89.8 | Active | 15.0 |
| 10 | 34.4 | Active | 5.0 |
|   | 20.9 | Inactive | 10.0 |
|   | 9.1 | Inactive | 15.0 |
| 11 | 78.2 | Active | 5.0 |
|   | 84.5 | Active | 10.0 |
|   | 89.2 | Active | 25.0 |
| 14 | 49.6 | Active | 5.0 |
|   | 65.9 | Active | 10.0 |
|   | 40.2 | Inactive | 15.0 |
| 12 | 81.8 | Active | 5.0 |
|   | 81.5 | Active | 10.0 |
|   | 37.5 | Inactive | 15.0 |
| 12 | 18.3 | Inactive | 5.0 |
|   | 27.7 | Inactive | 10.0 |
|   | 50.1 | Active | 15.0 |
| 15 | 36.0 | Active | 5.0 |
|   | 65.3 | Active | 10.0 |
|   | 84.3 | Active | 15.0 |
| 16 | 4.3 | Inactive | 5.0 |
|   | 32.7 | Inactive | 10.0 |
|   | 66.5 | Active | 15.0 |

TABLE II

SUMMARY OF IN VIVO DATA
Moderately Hypercholesterolemic Quail:

| Compound | Percent Change in Serum LDL Cholesterol From Control |
|---|---|
| Example 1 | −42% |
| Example 2 | −50% |
| Example 4 | −59% |

We claim:

1. A compound of the formula wherein $R_1$ is $C_4$ to $C_8$-cycloalkyl, $C_5$ to $C_{20}$-alkyl, $C_5$ to $C_{20}$-alkenyl, phenyl or phenyl-$C_1$ to $C_6$-alkyl;

$R_2$ is $C_1$ to $C_{20}$-alkyl, $C_5$ to $C_{20}$-alkenyl, phenylcarbonyl($C_1$ to $C_6$-alkyl)-, phenyl($C_1$ to $C_6$-alkyl), $C_1$ to $C_6$-alkyloxycarbonyl-$C_1$ to $C_6$-alkyl, (hydroxyimino)phenyl-($C_2$ to $C_6$-alkyl)-, (hydroxy)-phenyl($C_1$ to $C_6$-alkyl)-, or —$(CH_2)_n$-(phenyl)C=NOC(O)-G;

$R_3$ is hydrogen phenyl, or phenyl substituted with a halogen having an atomic number of from 9 to 35, hydroxy, $C_1$ to $C_6$-alkyl, $C_1$ to $C_6$-alkyloxy, or $C_2$ to $C_6$-alkenyl, $C_2$ to $C_6$-alkenyloxy;

$R_4$ is hydrogen, phenyl or phenyl substituted with a halogen having an atomic number of from 9 to 35, hydroxy, $C_1$ to $C_6$-alkyl, $C_1$ to $C_6$-alkyloxy, $C_2$ to $C_6$-alkenyl or $C_2$ to $C_6$-alkenyloxy, and G is $C_1$ to $C_{20}$-alkyl or $C_1$ to $C_{20}$-alkenyl;

m is 1 or 2;

n is 1 to 6; provided that when $R_3$ is a phenyl radical, $R_4$ is hydrogen, and when $R_4$ is other than hydrogen, $R_3$ is hydrogen.

2. A compound according to claim 1 wherein
$R_1$ is a $C_4$ to $C_8$-cycloalkyl,
$R_2$ is -phenyl($C_1$ to $C_3$-alkyl), phenylcarbonyl($C_1$ to $C_3$-alkyl) or —$(CH_2(_n$-(phenyl)C=NOC(O)-G;
$R_3$ is hydrogen,
$R_4$ is selected from the group consisting of phenyl and phenyl substituted with $C_1$ to $C_4$-alkyl, $C_1$ to $C_4$-alkyloxy, halogen, or hydroxy, and m is 1.

3. A compound according to claim 2, 6-cyclohexyl-6,7-dihydro-2-phenyl-4-(phenylmethyl)-4H-pyrazolo[1,5-a]pyrrolo[3,4-d]pyrimidine-5,8-dione.

4. A compound according to claim 2, 6-cyclohexyl-6,7-dihydro-2-(4-ethoxyphenyl)-4-(phenylmethyl)-4H-pyrazolo[1,5-a]pyrrolo[3,4-d]pyrimidine-5,8-dione.

5. A compound according to claim 2, 6-cyclohexyl-4-(phenylcarbonylmethyl)-2-(4-chlorophenyl)-6,7-dihydro-4H-pyrazolo[1,5-a]pyrrolo[3,4-d]pyrimidine-5,8-dione.

6. A compound according to claim 1 wherein
$R_1$ is phenyl or phenyl-$C_1$ to $C_3$-alkyl,
$R_2$ is a phenyl-$C_1$ to $C_3$-alkyl,
$R_3$ is hydrogen,
$R_4$ is phenyl or phenyl substituted with a $C_1$ to $C_4$-alkyl, $C_1$ to $C_4$-alkyloxy or a halogen having an atomic number of from 9 to 35 or hydroxy, and m is 1.

7. A compound according to claim 6, 4,6-bis(phenylmethyl))-6,7-dihydro-2-phenyl-4H-pyrazolo[1,5-a]pyrrolo[3,4-d]pyrimidine-5,8-dione.

8. A compound according to claim 1 wherein
$R_1$ is a $C_4$ to $C_8$-cycloalkyl,
$R_2$ is a phenyl-$C_1$ to $C_3$-alkyl,
$R_3$ is hydrogen,
$R_4$ is selected from the group consisting of phenyl and phenyl substituted with a $C_1$ to $C_4$-alkyl, $C_1$ to $C_4$-alkyloxy, a halogen or hydroxy, and m is 2.

9. A compound according to claim 8, 6-cyclohexyl-2-phenyl-4-(phenylmethyl)-5,6,7,8-tetrahydro-4H-pyrazolo[1,5-a]pyrido[3,4-d]pyrimidine-5,9-dione.

10. A compound according to claim 1 wherein
$R_1$ is $C_4$ to $C_8$-cycloalkyl,
$R_2$ is a phenyl-$C_1$ to $C_3$-alkyl,
$R_3$ is selected from the group consisting of phenyl and phenyl substituted with a $C_1$ to $C_4$-alkyl, $C_1$ to $C_4$-alkyloxy, hydroxy or a halogen, and
$R_4$ is hydrogen, and
m is 1.

11. A compound according to claim 10, 6-cyclohexyl-6,7-dihydro-3-phenyl-4-(phenylmethyl)-4H-pyrazolo[1,5-a]pyrrolo[3,4-d]pyrimidine-5,8-dione.

12. A compound according to claim 2 wherein $R_1$ is cyclohexyl, $R_2$ is —$(CH_2)_n$-(phenyl)C=NOC(O)-G, and $R_4$ is phenyl.

13. A compound according to claim 12, 6-cyclohexyl-6,7-dihydro-4-]2-{[(1-oxooctyl)oxy]imino]-2-phenylethyl}-4H-pyrazolo[1,5-a]pyrrole[3-4-d]pyrimidine-5-8-dione.

14. A compound according to claim 12, 6-cyclohexyl-6,7-dihydro-4-[2-{[(1-oxoheptyl)oxy]imino}-2-phenylethyl]-2-phenyl-4H-pyrazolo[1,5-a]pyrrolo[3,4-d]pyrimidine-5,8-dione, less polar isomer.

15. A compound according to claim 12, 6-cyclohexyl-6,7-dihydro-4-[2-{[(1-oxoheptyl)oxy]imino}-2-phenylethyl]-2-phenyl-4H-pyrazolo[1,5-a]pyrrolo[3,4-d]pyrimidine-5,8-dione, more polar isomer.

16. A compound according to claim 12, 6-cyclohexyl-6,7-dihydro-4-[2-{[(1-oxododecyl)oxy]imino}-2-phenylethyl[-2-phenyl-4H-pyrazolo[1,5-a]pyrrolo[3,4-d]pyrimidine-5-8-dione.

* * * * *